(12) United States Patent
Crespin et al.

(10) Patent No.: US 8,536,173 B2
(45) Date of Patent: Sep. 17, 2013

(54) TETRAHYDROQUINOXALINE UREA DERIVATIVES AS MODULATORS OF 11-B-HYDROXYSTEROID DEHYDROGENASE TYPE I

(75) Inventors: Olivier Crespin, Paris (FR); Eric Nicolai, Paris (FR); Olivier Venier, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/386,830

(22) PCT Filed: Jul. 23, 2010

(86) PCT No.: PCT/FR2010/051563
§ 371 (c)(1),
(2), (4) Date: Mar. 14, 2012

(87) PCT Pub. No.: WO2011/012800
PCT Pub. Date: Feb. 3, 2011

(65) Prior Publication Data
US 2012/0165337 A1    Jun. 28, 2012

(30) Foreign Application Priority Data
Jul. 27, 2009   (FR) ..................... 09 03685

(51) Int. Cl.
*A61K 31/495*   (2006.01)
(52) U.S. Cl.
USPC ........ 514/249; 544/355; 544/359; 546/268.1; 548/131; 548/250
(58) Field of Classification Search
USPC .............. 514/249; 544/355, 359; 546/268.1; 548/131, 250
See application file for complete search history.

(56) References Cited

FOREIGN PATENT DOCUMENTS

| CA | 2713367 | * | 9/2009 |
|---|---|---|---|
| WO | WO2008/000950 A2 | | 1/2008 |
| WO | WO2008/000951 A2 | | 1/2008 |
| WO | WO2009/112691 A2 | | 9/2009 |

OTHER PUBLICATIONS

Jordan, V. C. Nature Reviews: Drug Discovery, 2, 2003, 205.*
Hackam, et al. JAMA, 296(14), 2006, 1731-1732.*
Vippagunta, et al. Advanced Drug Delivery Reviews, 48, 2001, 18.*
International Preliminary Report on Patentability dated Mar. 6, 2012 issued in PCT/FR2010/051563.
Hughes, Katherine A. et al., "11-Beta-hydroxysteroid dehydrogenase type 1 (11B-HSD1)inhibitors in Type 2 diabetes mellitus and obesity," Expert Opinion Investigational Drugs (2008), vol. 17, No. 4, pp. 481-496.
Saiah, Eddine, "The Role of 11Beta-Hydroxysteroid Dehydrogenase in Metabolic Disease and Therapeutic Potential of 11Beta-HSD1 Inhibitors," Current Medicinal Chemistry (2008), vol. 15, pp. 642-649.
International Search Report dated Oct. 15, 2010 issued in PCT/FR2010/051563.

* cited by examiner

*Primary Examiner* — Douglas M Willis
(74) *Attorney, Agent, or Firm* — Scully, Scott, Murphy & Presser, P.C.

(57) ABSTRACT

The invention relates to compounds of formula (I),

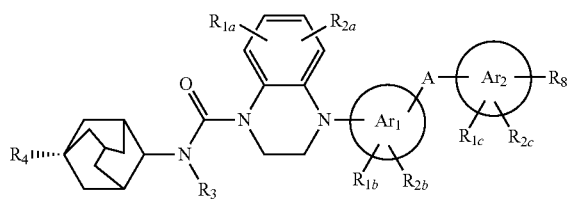

where A, $Ar_1$, $Ar_2$, $R_{1a}$, $R_{1b}$, $R_{1c}$, $R_{2a}$, $R_{2b}$, $R_{2c}$, $R_3$, $R_4$ and $R_8$ are as described herein, and pharmaceutical compositions thereof, methods of preparation thereof, and methods of use thereof.

23 Claims, No Drawings

TETRAHYDROQUINOXALINE UREA DERIVATIVES AS MODULATORS OF 11-B-HYDROXYSTEROID DEHYDROGENASE TYPE I

The present invention relates to tetrahydroquinoxaline urea derivatives, preparation thereof, and therapeutic use thereof.

The compounds according to the invention modulate the activity of 11β-hydroxysteroid dehydrogenase type 1 (11βHSD1) and are useful for treating pathologies in which such modulation is beneficial, as in the case of metabolic syndrome or of noninsulin-dependent type 2 diabetes.

11βHSD1 locally catalyzes the conversion of inactive glucocorticoids (cortisone in humans) to active glucocorticoids (cortisol in humans) in various tissues and organs, principally the liver and adipose tissue, but also in muscles, bone, pancreas, endothelium, ocular tissue and in certain parts of the central nervous system. 11βHSD1 acts as a regulator of the action of glucocorticoids in the tissues and organs where it is expressed (Tomlinson et al., *Endocrine Reviews* 25(5), 831-866 (2004), Davani et al., *J. Biol. Chem.* 275, 34841 (2000); Moisan et al., *Endocrinology,* 127, 1450 (1990)).

The principal pathologies in which glucocorticoids and inhibition of 11βHSD1 are involved are stated below.

A. Obesity, Type 2 Diabetes and Metabolic Syndrome

The role of 11βHSD1 in obesity, type 2 diabetes and metabolic syndrome (also known as syndrome X or insulin resistance syndrome) where the symptoms include visceral obesity, glucose intolerance, insulin resistance, hypertension, type 2 diabetes and hyperlipidemia (*Reaven Ann. Rev. Med.* 44, 121 (1993)) is described in many works. In humans, treatment with carbenoxolone (a nonspecific inhibitor of 11βHSD1) improves insulin sensitivity in slender volunteer patients and in patients with type 2 diabetes (Andrews et al., *J. Clin. Endocrinol. Metab.* 88, 285 (2003)). Moreover, mice whose gene for 11βHSD1 has been turned off are resistant to hyperglycemia induced by stress and obesity, show attenuation of the induction of liver enzymes of neoglucogenesis (PEPCK and G6P) and display an increase in insulin sensitivity in adipose tissue (Kotelevstev et al., *Proc. Nat. Acad. Sci.* 94, 14924 (1997); Morton et al., *J. Biol. Chem.* 276, 41293 (2001)). Moreover, transgenic mice in which the gene for 11βHSD1 has been overexpressed in adipose tissues have a phenotype similar to that of human metabolic syndrome (Masuzaki et al., Science 294, 2166 (2001)). It should be noted that the phenotype observed exists without an increase in total circulating glucocorticoids, but is induced by specific increase in active glucocorticoids in the adipose deposits. Furthermore, new classes of specific inhibitors of 11βHSD1 have appeared recently:

arylsulfonamidothiazoles have been shown to improve insulin sensitivity and reduce the level of glucose in the blood of mice with hyperglycemia (Barf et al., *J. Med. Chem.* 45, 3813 (2002)). Moreover, it was shown in a recent study that compounds of this type reduced food intake as well as weight gain in obese mice (Wang et al. *Diabetologia* 49, 1333 (2006));

triazoles have been shown to improve metabolic syndrome and slow the progression of atherosclerosis in mice (Hermanowski-Vosatka et al., *J. Exp. Med.* 202, 517 (2005)).

A2. Microvascular Complications of Diabetes

The presence of chronic complications in patients with type 2 diabetes is often linked to the severity and duration of diabetes. Functional and structural microvascular disorders largely explain the development of certain pathologies observed in diabetic patients such as neuropathy, retinopathy, and nephropathy (Rayman, Diabetes Review 7:261-274, 1999; Gärtner and Eigentler, Clin Nephrol 70:1-9, 2008; Zent and Pozzi, Sem Nephrol 27:161-171, 2007; Malecki et al., EJCI38:925-930, 2008). Chronic increase in glycemia, or glucose intolerance, represent major risk factors of these microvascular complications (Robinson Singleton et al. Diabetes 52:2867-2873, 2003; Lachin et al. Diabetes 57: 995-1001, 2008). By providing better control of glycemia, through a decrease in hepatic neoglucogenesis and an increase in the body's insulin sensitivity (see chapter "obesity, type 2 diabetes and metabolic syndrome"), inhibitors of 11βHSD1 can prevent progression to the microvascular complications observed in diabetic patients. However, strict control of glycemia cannot completely prevent the development of microvascular complications, and it is therefore necessary to discover new treatments for more general treatment of diabetic and dyslipidemic patients (Girach et al. Int J Clin Pract 60(11): 1471-1483, 2006; Taylor. Curr Diab Rep 8 (5): 345-352; 2008). Interestingly, a study by Chiodini et al. (Diabetes Care 30: 83-88, 2007) showed that cortisol secretion in diabetic patients was linked directly to the presence of chronic macrovascular or microvascular complications. Moreover, microvascular reactivity and endothelial function are altered in patients with Cushing syndrome who have hypercortisolism (Prazny et al. Physiol Rev 57:13-22, 2008).

More particularly, Bhatia et al. (Ann Ophthalmol 15:128-130; 1983) demonstrated a link between raised plasma cortisol levels and retinopathy in diabetic patients.

Koh et al. showed that treatment of patients with Cushing syndrome by adrenalectomy, making it possible to reverse hypercortisolism, improves renal function.

The clinical parameters of polyneuropathies (sensory perception, cardiac autonomic neuropathy) are associated with an increase in cortisol secretion in diabetic patients (Tsigos et al. J Clin Endocrinol Metab 76:554-558, 1993).

All these elements show that a decrease in the impact of cortisol by local inhibition of its regeneration, via inhibitors of 11βHSD1, could have a favorable role in microcirculatory disorders associated with diabetes (polyneuropathy, retinopathy, and nephropathy).

B. Cognition and Dementia

Mild cognitive disorders are phenomena that are common to the elderly and to type 1 and 2 diabetics, and can gradually lead to depression or dementia (Messier et al., *Neurobiol. aging* 26, 26; Greenwood et al. (2005), *Neurobiol. aging* 26, 45 (2005)). Both in older animals and older humans, interindividual differences for general cognitive functions have been linked to differences in long-term exposure to glucocorticoids (Lupien et al., *Nat. Neurosci.* 1, 69, (1998)). Moreover, deregulation of the HPA (hypothalamic-pituitary-adrenal) axis, resulting in chronic exposure of certain sub-regions of the brain to glucocorticoids has been suggested as contributing to the decline of cognitive functions (McEwen et al., *Curr. Opin. Neurobiol.* 5, 205, 1995). 11βHSD1 is abundant in the brain and is expressed in many sub-regions including the hypothalamus, the frontal cortex and the cerebellum (Sandeep et al., *Proc. Natl. Acad. Sci.* 101, 6734 (2004)). Mice deficient in 11βHSD1 are protected against the dysfunctions of the hypothalamus associated with glucocorticoids that are linked to old age (Yau et al., *Proc. Natl. Acad. Sci.* 98, 4716, (2001)). Moreover, in studies in humans, it has been shown that administration of carbenoxolone improves verbal fluency and verbal memory in the elderly (Yau et al.,

*Proc. Natl. Acad. Sci.* 98, 4716 (2001), Sandeep et al., *Proc. Natl. Acad. Sci.* 101, 6734 (2004)). Finally, the use of selective inhibitors of 11βHSD1 of the triazole type has shown that they prolong memory retention in older mice (Rocha et al., Abstract 231 *ACS meeting*, Atlanta, 26-30 Mar. 2006). Moreover, it was shown in diabetic rodent models that the corticosterone level contributed to the development of cognitive pathologies induced by diabetes (Stranhan et al., Nature neurosc. 11, 309 (2008)). Thus, inhibitors of 11βHSD1, by allowing a reduction in cortisol regeneration in the hippocampus, could have a beneficial effect on cognitive functions in elderly diabetic patients (Sandeep et al., *Proc. Natl. Acad. Sci.* 101, 6734 (2004)).

C. Intraocular Pressure

Glucocorticoids can be used topically or systemically for a wide range of pathologies of clinical ophthalmology. A particular complication of these treatments is glaucoma induced by the use of corticosteroids. This pathology is characterized by increase in intraocular pressure (IOP). In the most severe cases and for untreated forms, IOP can lead to a partial loss of visual field and possibly to complete loss of sight. IOP is the result of an imbalance between production of aqueous humor and drainage thereof. The aqueous humor is produced in nonpigmented epithelial cells and drainage is performed by the cells of the trabecular network. 11βHSD1 is localized in the nonpigmented epithelial cells and its function is clearly amplification of the activity of glucocorticoids in these cells (Stokes et al., *Invest. Ophthalmol. Vis. Sci.* 41, 1629 (2000)). This concept is confirmed by the observation that the concentration of free cortisol is greatly in excess relative to cortisone in the aqueous humor. (ratio 14/1). The functional activity of 11βHSD1 in the eyes was evaluated by studying the effects of carbenoxolone in healthy volunteers. After seven days of treatment with carbenoxolone, IOP is reduced by 18% (Rauz et al., *Invest. Ophtamol. Vis. Sci.* 42, 2037 (2001)). The inhibition of 11βHSD1 in the eyes is therefore predicted as reducing the local concentration of glucocorticoids and the IOP, producing a beneficial effect in the treatment of glaucoma and other disorders of vision.

D. Hypertension

Hypertensive substances from the adipocytes such as leptin and angiotensinogen have been suggested as being key elements in obesity-related hypertension pathologies (Wajchenberg et al., *Endocr. Rev.* 21, 697 (2000)). Leptin, which is secreted in excess in aP2-11βHSD1 transgenic mice (Masuzaki et al., *J. Clinical Invest.* 112, 83 (2003)), can activate various networks of sympathetic neuronal systems, including those that regulate arterial pressure (Matsuzawa et al., *Acad. Sci.* 892, 146 (1999)). Moreover, the renin-angiotensin system (RAS) has been identified as being a determining pathway in the variation of arterial pressure. Angiotensinogen, which is produced in the liver and in adipose tissue, is a key substrate for renin and is at the origin of activation of the RAS. The plasma angiotensinogen level is significantly raised in aP2-11βHSD1 transgenic mice, as are those of angiotensin II and of aldosterone (Masuzaki et al., *J. Clinical Invest.* 112, 83 (2003)); these elements lead to the increase in arterial pressure. Treating these mice with low doses of an angiotensin II receptor antagonist eliminates this hypertension (Masuzaki et al., *J. Clinical Invest.* 112, 83 (2003)). These data illustrate the importance of local activation of glucocorticoids in adipose tissue and in the liver, and suggests that this hypertension may be caused or exacerbated by the activity of 11βHSD1 in these tissues. Inhibition of 11βHSD1 and reduction of the level of glucocorticoids in adipose tissue and/or in the liver is therefore predicted as having a beneficial role for the treatment of hypertension and of related cardiovascular disorders.

D2. Salt-Sensitive Arterial Hypertension

It is estimated that about 30 to 50% of the general population are particularly sensitive to salt. There is a wealth of evidence suggesting a link between sensitivity to salt and arterial hypertension and cardiovascular risks (Weinberger M H, Curr Opin Cardiol 2004; 19:353-356). It has been shown that salt-sensitive subjects have a decreased variability of heart rate, as well as increased arterial pressure and cortisol production during mental stress, compared with subjects who are not sensitive (Weber C S et al., Journal of Human Hypertension 2008; 22:423-431). Moreover, a recent study by Liu Y et al. (Physiol Genomics 2008 Sep. 30) demonstrated in the Dahl salt-sensitive rat that specific inhibition of expression of renal medulla 11βHSD1, by the use of shRNA, can greatly reduce, in animals, the increase in mean arterial pressure induced by a salty diet. These elements suggest that an inhibitor of the enzyme 11βHSD1 would very probably have a beneficial effect on this form of arterial hypertension.

E. Osteoporosis

The development of the skeleton and the osseous functions are also regulated by the action of glucocorticoids. 11βHSD1 is present in osteoclasts and osteoblasts. Treatment of healthy volunteers with carbenoxolone showed a decrease in markers of bone resorption without a change in the markers of bone formation (Cooper et al., Bone, 27, 375 (2000)). Inhibition of 11βHSD1 and reduction of the level of glucocorticoids in the bones could therefore be used as a protective mechanism in the treatment of osteoporosis.

F. Lipodystrophy Associated with Highly Active Antiretroviral Therapy (HAART), or HAL Syndrome The use of intensive antiretroviral treatment for AIDS patients often induces a lipodystrophy syndrome (HAL) resembling Cushing syndrome, and associating increase in abdominal fat mass, hypertriglyceridemia and insulin resistance. It has been shown (Sutinen et al., Diabetologia, 47, 1668 (2004)) that this lipodystrophy (HAL) is associated with an increase in expression of 11βHSD1 in patients' adipose tissue. Inhibitors of 11βHSD1, allowing a reduction of cortisol regeneration in the adipose tissue, could therefore have a beneficial role in patients with lipodystrophy associated with intensive treatment of AIDS with antiretrovirals (HAL syndrome).

G. Infectious Diseases

Certain infections, such as tuberculosis, are associated with disorders of the immune response (Ellner J J, J. Lab. Clin. Med, 130, 469, (1997)). This feature, which is most often accompanied by an increase in secretion of certain cytokines (IL-10, TNFα) and/or response to certain cytokines, seems to be caused, at least partly, by local tissue exposure of the immune cells to glucocorticoids. Moreover, the administration of synthetic glucocorticoids in humans or animals causes reactivation of tuberculosis in humans and in animals (Haanas O C et al. Eur. J. Respir. Dis. 64, 294 (1998), Brown et al. Infect. Immun. 63, 2243, (1995)). Moreover, various stresses that are activators of the HPA axis lead to reactivation of said infection.

Apart from these particular cases, circulating glucocorticoid levels as well as activation of the HPA axis seem to be normal in patients with tuberculosis (Baker et al. Am. J. Resp. Crit. Care. Med., 162, 1641 (2000)). In contrast, the levels of cortisol versus cortisone in the bronchoalveolar fluid seem to be raised, reflecting a modulation of glucocorticoid metabolism to the active form (notably dependent on the activity of 11βHSD1). Inhibition of 11βHSD1 in the peripheral tissues and notably the lungs might consequently produce a beneficial effect on stabilization and then reversion of infection.

H. Cardiac Hypertrophy and Heart Failure

Cardiovascular diseases represent the primary cause of morbidity and mortality in industrialized countries, and left ventricular hypertrophy (LVH) is an independent risk factor of cardiovascular mortality (Havranek E P, Am J Med 121:870-875, 2008). Aside from genetic causes, pathological conditions such as arterial hypertension, myocardial infarction, or renal insufficiency can lead to a compensatory hypertrophy, subsequently progressing to chronic heart failure. 11βHSD1 activity, permitting conversion of 11-dehydrocorticosterone to corticosterone, is expressed in the cardiomyocytes of newborn rats, and contributes to the modulating activity of glucocorticoids and aldosterone in the heart (Sheppard and Autelitano, Endocrinology 143:198-204, 2002). Using these cells, Lister et al. (Cardiovascular Research 70: 555-565, 2006) showed that drug-induced hypertrophy of the cardiomyocytes is accompanied by an increase in activity of the enzyme 11βHSD1. In this same study, the use of RU-486, a specific antagonist of the glucocorticoid receptors, made it possible to reduce the hypertrophy of the cells.

Inhibitors of 11βHSD1 activity might therefore limit cardiac hypertrophy and thus prevent progression to heart failure.

I. Liver Diseases:

I1. Hepatic Steatosis:

Studies in severely obese patients (BMI>35 kg/m2) report a prevalence of 91% for steatosis and of 37% for steatohepatitis (*Neuschwander-Tetri & Caldwell, Hepatology,* 37, 1202-1219, 2003). Type 2 diabetes is another major factor associated with steatosis with a prevalence of 70% reported for a sample of 3000 Italian diabetics (Targher et al., *Diabetes Care,* 30, 1212-1218, 2007). Moreover, a link has been observed between insulin resistance and hepatic steatosis independently of obesity in patients with nonalcoholic hepatic steatosis (Manchesini et al., *Diabetes,* 50, 1844-1850, 2001). In obese patients, 11βHSD1 activity appears to be modified, as indicated by the activation of orally administered cortisone, urinary excretion of cortisol metabolites or hepatic tissue expression of 11βHSD1. (Tomlinson et al., *Endocrine Rev,* 25, 831-866, 2004; Rask et al., *J. Clin. Endocrin. Metab.,* 86, 1418-1421, 2001; Stewart et al., *J. Clin. Endocrin. Metabol.* 84, 1022-1027, 1999; Valsamakis et al., *J. Clin. Endocrinol. Metabol.,* 89, 4755-4761, 2004). Transgenic mice overexpressing 11βHSD1 in the adipose tissue or in the liver develop hepatic steatosis and dyslipidemia (Masuzaki et al., *Sciences* 294, 2166-2170, 2001; Paterson et al., *PNAS,* 101, 7088-7093, 2004). Inhibition of 11βHSD1 in rats reduces fasting triglyceridemia following a decrease in secretion of hepatic triglycerides and an increase in capture and tissue oxidation of fatty acids, which is also reflected in the liver by a significant decrease in triglycerides (Berthiaume et al., *Am. J. Physiol. Endocrinol. Metab.,* 293, 1045-1052, 2007). Local reduction of active glucocorticoid by inhibition of 11βHSD1 activity is therefore envisaged for reducing the insulin-resistant and lipid effects of glucocorticoids and thus reducing hepatic steatosis.

I2. Metabolic Steatohepatitis:

Metabolic steatohepatitis represents a stage of development of metabolic hepatic steatosis in some people. A correlation has been described between urinary cortisol, post-dexamethasone cortisol concentration and the grade of necroinflammation and hepatic fibrosis in subjects with metabolic steatohepatitis suggesting the existence of subclinical or local hypercorticolism (Targher et al., *Clin. Endocrinol.,* 64, 337-341, 2006). A general and local correction (at centrilobular level) of insulin resistance, and an improvement in oxidation of hepatic fatty acids by inhibition of 11βHSD1 activity, as well as reduction of the pro-fibrotic effects of cortisol, are therefore predictive of an improvement of the pathological evolution.

I3. Hepatic Regeneration:

The liver has a considerable capacity for regeneration, completely necessary in the case of injuries whether or not of infectious origin, in particular arising from the digestive tract. For example, hepatic apoptosis or necrosis can result from drug-induced, viral, alcoholic, metabolic, cholestatic or vascular ischemic toxicity. Glucocorticoids inhibit hepatocyte proliferation and hepatic tissue regeneration (Tsukamoto & Kojo, *Gut,* 30, 387-390, 1989; Nagy et al., *Hepatology,* 28, 423-429, 1998; Tannuri et al., *Pediatr. Transplantation,* 12, 73-79, 2008). Inhibition of 11βHSD1 reductase activity could in this context lessen the negative local effects of cortisol on hepatic regeneration and are to be aligned with the pro-angiogenic effects of these inhibitors and with their positive action on certain growth factors.

J. Healing of Chronic Skin Wounds:

The healing of chronic wounds depends on the underlying pathological context which modifies and desynchronizes the physiological stages of healing. In chronic diabetic ulcers, the potential benefit of inhibitors of 11βHSD1 is to be seen both in correction of the manifestations of diabetes, taking into account the local pathological role of endogenous corticoids at the level of the wound and the state of pathological progression. There is some evidence showing that endogenous corticoids are directly involved in the alteration of wound healing in humans and in rodent animal models (Goforth et al., *J. Foot Surgery,* 19, 199-2002, 1980; Dostal et al., *Arch. Surg.,* 125, 636-640, 1990; Bitard, *Am. J. Pathology,* 152, 547-554, 1998). Local production of cortisol is predicted by the presence of 11βHSD1 reductase activity at endothelial, fibroblastic, and cutaneous level in humans and in rodents (Gong et al., *Steroids* 73, 1187-1196, 2008; Hammami et al., *J. Clin. Endocrinol. Metabol.,* 73, 326-334, 1991; Cooper et al., *ENDO* 2003; Teelucksingh et al., *Lancet,* 335, 1060-1063, 1990). Cortisol and other glucocorticoids inhibit skin ulcer healing by many mechanisms and at different stages: alteration of microcirculatory vasomotor activity, inhibition of the inflammatory phase in particular on the synthesis of prostaglandins, of leukotrienes, of cytokines, such as TNFalpha and production of IL-1beta, IL-4, etc. and signalling of IFNgamma, increase of infection, reduction of cellular motility and proliferation of keratinocytes, reduction of expression of pro-angiogenic factors such as VEGF, suppression of expression of TGFbeta 1 and 2 that are essential in the production of collagen by the fibroblasts and their transformation into myofibroblasts, suppression of expression of MMP1, 2, 9 and 10 and induction of TIMP thus blocking remodelling, promotion of terminal epidermal differentiation but inhibition of the first stages of differentiation, causing fragility of the epidermis (Bitard, *Am. J. Pathology,* 152, 547-554, 1998, Beer et al., *Vitam. Horm.,* 59, 217-239, 2000; Rosen & Miner, *Endocrine Review,* 26, 452-464, 2005, Stojadinovic et al., *J. Biol. Chem.,* 282, 4021-4034, 2007). Conversely, and as expected, inhibition of 11βHSD1 reductase activity is described as inducing vasodilatation, a pro-angiogenic and anti-infectious effect (see the corresponding chapters) and in certain inflammatory situations, producing exacerbation and growth factor overexpression such as TGF-beta (Zhang et al., *J. Immunology*, 179, 6325-6335, 2007). Inhibitors of 11βHSD1 should therefore, based on this action, improve the healing of chronic skin wounds.

BRIEF SUMMARY OF THE INVENTION

Tetrahydroquinoxaline urea derivatives have now been found, which have an adamantane nucleus, and which modulate the activity of 11βHSD1.

DETAILED DESCRIPTION OF THE INVENTION

The present invention relates to compounds corresponding to formula (I):

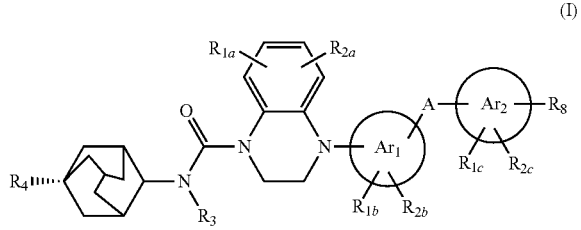

in which:
A represents a bond, an oxygen atom or an —O—CH$_2$— group,
Ar$_1$ represents a phenyl or heteroaryl group,
Ar$_2$ represents a phenyl group, a heteroaryl group or a heterocycloalkyl group,
R$_{1a,b,c}$ and R$_{2a,b,c}$, which may be identical or different, each represent a hydrogen or halogen atom or an alkyl, cycloalkyl, -alkyl-cycloalkyl group, optionally substituted with one or more halogen atoms; —OR$_5$ (hydroxy or alkoxy); hydroxy-alkyl; alkoxy-alkyl; alkoxy-alkoxy; haloalkyl; —O-haloalkyl; oxo; —CO-alkyl; —CO-alkyl-NR$_6$R$_7$; —CO-haloalkyl; —COOR$_5$; alkyl-COOR$_5$; —O-alkyl-COOR$_5$; —SO$_2$-alkyl; —SO$_2$-cycloalkyl; —SO$_2$-alkyl-cycloalkyl; —SO$_2$-alkyl-OR$_5$; —SO$_2$-alkyl-COOR$_5$; —SO$_2$-alkyl-NR$_6$R$_7$; —SO$_2$-haloalkyl; alkyl-SO$_2$-alkyl; —SO$_2$—NR$_6$R$_7$; —SO$_2$-alkyl-alkoxy-alkoxy; —CONR$_6$R$_7$; -alkyl-CONR$_6$R$_7$ or —O-alkyl-NR$_6$R$_7$, or R$_{1a}$, R$_{1b}$, R$_{1c}$ are bound respectively to R$_{2a}$, R$_{2b}$, R$_{2c}$ and to the carbon atom that bears them and represent —O-alkyl-O—;
R$_3$ represents a hydrogen atom or an alkyl group,
R$_4$ represents a —CONR$_6$R$_7$ group; hydroxy-alkyl substituted with a haloalkyl group; -alkyl-NH—SO$_2$-alkyl; —NH—SO$_2$-alkyl; —O—SO$_2$—NR$_6$R$_7$; -alkyl-CO—NR$_6$R$_7$; —O-alkyl-CO—NR$_6$R$_7$; -alkyl-NR$_6$R$_7$; —O—CO—NR$_6$R$_7$; alkyl-heteroaryl; heteroaryl optionally substituted with an alkyl group; alkoxy-imino; —CO—NH—NH—CO-alkyl; provided that R$_4$ is in cis position when it represents the group —CONR$_6$R$_7$ and that R$_6$ and R$_7$ each represent hydrogen, an -alkyl or -alkyl-phenyl group;
R$_5$ represent hydrogen, an alkyl group or an -alkyl-phenyl group;

R$_6$ and R$_7$, which may be identical or different, each represent a hydrogen atom, an alkyl or alkoxy group or an -alkyl-phenyl group, and
R$_8$ represents a hydrogen atom, an alkyl group or a group of formula —B-Het, where B can be absent or can represent a bond, an oxygen atom or a —CO— or —SO$_2$—(CH$_2$)$_n$ group with n equal to 0, 1 or 2 and where Het represents a heteroaryl or a heterocycloalkyl optionally substituted with 1 to 3 groups selected from the alkyl, —SO$_2$-alkyl and —COOR$_5$ groups.

The compounds of formula (I) can have one or more asymmetric carbon atoms. They can therefore exist in the form of enantiomers or of diastereoisomers. These enantiomers, diastereoisomers, and mixtures thereof, including the racemic mixtures, form part of the invention.

The compounds of formula (I) can be in the form of bases or of acids or can be salified by acids or bases, notably pharmaceutically acceptable acids or bases. These salts of addition form part of the invention. These salts are advantageously prepared with pharmaceutically acceptable acids or bases, but salts of other acids or bases that can be used, for example, for purifying or isolating the compounds of formula (I), also form part of the invention.

The compounds of formula (I) can also exist in the form of hydrates or solvates, namely in the form of associations or combinations with one or more solvent molecules. These solvates also form part of the invention.

In the context of the present invention, and unless stated otherwise in the text, the terms used have the following meanings:
a halogen atom: a fluorine, a chlorine, a bromine or an iodine;
an alkyl group: a saturated, linear or branched aliphatic group having from 1 to 5 carbon atoms. As examples, we may mention the methyl, ethyl, propyl, methylpropyl, isopropyl, butyl, isobutyl, tertbutyl or pentyl groups;
a cycloalkyl group: a cyclic alkyl group having from 3 to 6 carbon atoms. As examples, we may mention the cyclopropyl, cyclobutyl, cyclopentyl groups;
an alkoxy group: a radical of formula —O-alkyl, where the alkyl group is as defined above;
a hydroxy-alkyl group: a radical of formula alkyl-OH, where the alkyl group is as defined above;
an alkoxy-alkyl group: a radical of formula alkyl-O-alkyl, where the alkyl groups, which may be identical or different, are as defined above. As examples, we may mention —(CH$_2$)$_2$—O—CH$_3$, —(CH$_2$)$_3$—O—CH$_3$, —CH—(CH$_2$—O—CH$_3$)$_2$;
an alkoxy-alkoxy group: a radical of formula —O-alkyl-O-alkyl, where the alkyl groups, which may be identical or different, are as defined above;
a haloalkyl group (abbreviated to Hal-alkyl): an alkyl group as defined above substituted with 1 to 5 halogen atoms, as defined above. We may mention for example the trifluoromethyl group;
a heteroaryl group: an aromatic group comprising 5 to 9 atoms, including 1 to 4 heteroatoms, such as nitrogen, oxygen or sulfur. We may notably mention the pyridinyl, pyrimidinyl, pyridazinyl, thiazolyl, tetrazole, or oxadiazole groups; and
a heterocycloalkyl: a mono-, bi-cyclic alkyl group, optionally bridged, having from 4 to 9 atoms or optionally partially unsaturated and of which 1 or 2 atoms are heteroatoms, such as oxygen, nitrogen or sulfur. We may notably mention the pyrrolidinyl, piperidinyl, piperazinyl, tetrahydropyranyl, morpholinyl, homopiperazinyl, 3,8-diazabicyclo[3.2.1]octane, thiomorpholinyl and thiomorpholinyl-1,1-dioxide, octahydro-pyrrolo[3,4-c] pyrrole, 1,2,3,6-tetrahydro-pyridine, 2,5-diaza-bicyclo [2.2.1]heptane groups;

a carbonyl function is represented by CO.

In the context of the present invention, $R_{1a,b,c}$ denotes the groups $R_{1a}$, $R_{1b}$ and $R_{1c}$ and $R_{2a,b,c}$ denotes the groups $R_{2a}$, $R_{2b}$ and $R_{2c}$. When $Ar_2$ represents a heterocycloalkyl group, the groups $R_{1c}$, $R_{2c}$ and $R_8$ can be carried by any atom of said heterocycle, whether it is a carbon atom or a heteroatom (for example a nitrogen atom), including by the same atom of said heterocycloalkyl (for example when it is a sulfur atom).

In the compounds of formula (I) according to the invention, the group $R_4$ and the urea group can, unless stated otherwise, be in trans position or in cis position. The compounds of formula (I) in which $R_4$ and the urea group are in trans position are particularly preferred.

Among the compounds of formula (I) according to the invention, we may mention a subgroup of compounds in which A represents a bond.

Another subgroup of compounds of formula (I) according to the invention is such that $Ar_1$ represents a heteroaryl group. Advantageously, $Ar_1$ represents a pyridinyl group.

Another subgroup of compounds of formula (I) according to the invention is such that $Ar_2$ represents a heterocycloalkyl group.

Another subgroup of compounds of formula (I) according to the invention is such that $Ar_2$ represents piperazinyl, homopiperazinyl, 3,8-diazabicyclo[3.2.1]octane, morpholinyl, thiomorpholinyl, octahydro-pyrrolo[3,4-c]pyrrole, 1,2,3,6-tetrahydro-pyridine or 2,5-diaza-bicyclo[2.2.1]heptane. Advantageously, $Ar_2$ represents a piperazinyl group.

Among the compounds of formula (I) according to the invention in which $Ar_1$ represents a heteroaryl group with 6 ring members, we may mention those in which the bond between the nuclei $A-Ar_2$ and $Ar_1$ is in para position relative to the bond between $Ar_1$ and the nitrogen atom of the tetrahydroquinoxaline nucleus to which it is bound.

Among the compounds of formula (I) according to the invention in which $Ar_2$ represents a heterocycloalkyl group, we may mention those which are bound to group A by a heteroatom.

Another subgroup of compounds of formula (I) according to the invention is such that $R_{1a}$, $R_{2a}$, $R_{1b}$ and $R_{2b}$ each represent a hydrogen atom.

Another subgroup of compounds of formula (I) according to the invention is such that $R_{1c}$ and $R_{2c}$, which may be identical or different, each represent a hydrogen or halogen atom or an alkyl, or —$SO_2$-cycloalkyl group.

Another subgroup of compounds of formula (I) according to the invention is such that $R_{1a,b}$ and $R_{2a,b,c}$ each represent a hydrogen atom and $R_{1c}$ represents hydrogen, an alkyl or —$SO_2$-cycloalkyl group.

Another subgroup of compounds of formula (I) according to the invention is such that $R_3$ represents a hydrogen atom.

Another subgroup of compounds of formula (I) according to the invention is such that $R_8$ represents a hydrogen atom, or a group of formula —B-Het, where B is absent and Het represents a tetrahydropyranyl group.

The subgroups defined above taken separately or in combination also form part of the invention.

A group of compounds of formula (I) particularly preferred in the sense of the invention consists of the compounds of formula (I) in which:

A is a direct bond;
$Ar_1$ is a heteroaryl;
$Ar_2$ is a heterocycloalkyl;
$R_3$ represents a hydrogen atom or an alkyl, $R_4$ represents a —$CONR_6R_7$ group; hydroxy-alkyl substituted with a haloalkyl group; -alkyl-NH—$SO_2$-alkyl; —NH—$SO_2$-alkyl; —O—$SO_2$—$NR_6R_7$; -alkyl-CO—$NR_6R_7$; —O-alkyl-CO—$NR_6R_7$; -alkyl-$NR_6R_7$; —O—CO—$NR_6R_7$; alkyl-heteroaryl; heteroaryl optionally substituted with an alkyl group; alkoxy-imino; —CO—NH—NH—CO-alkyl; provided that $R_4$ is in cis position when it represents the —$CONR_6R_7$ group and that $R_6$ and $R_7$ each represent hydrogen, an -alkyl or -alkyl-phenyl group;

$R_5$ represent hydrogen, an alkyl group or an -alkyl-phenyl group;

$R_6$ and $R_7$, which may be identical or different, each represent a hydrogen atom, an alkyl or alkoxy group or an -alkyl-phenyl group, and $R_8$ represents a hydrogen atom, an alkyl group or a tetrahydropyranyl group.

Among the above compounds, those are particularly preferred in which $R_{1a,b,c}$ and $R_{2a,b,c}$ are hydrogen and $R_8$ is an alkyl or tetrahydropyranyl group and those in which $R_{1a,b,c}$ and $R_{2a,b}$ and $R_8$ are hydrogen and $R_{2c}$ is an alkyl or —$SO_2$-cycloalkyl group, in which the cycloalkyl group is preferably the cyclopropyl group.

Another subgroup of compounds of formula (I) according to the invention is such that $R_4$ represents a group: —$CONH_2$; hydroxymethyl substituted with a trifluoromethyl group; —$CH_2NH$—$SO_2$-Me; —NH—$SO_2$-Me; —$CH_2$—CO—$NH_2$; —$CH_2$—$NH_2$; —$OCONH_2$; —CONH—OMe; tetrazolylmethyl and methyloxadiazolyl.

Among the compounds of formula (I) according to the invention, we may notably mention the following compounds:

cis 4-{5-[4-(Tetrahydro-pyran-4-yl)piperazin-1-yl]pyridin-2-yl}-3,4-dihydro-2H-quinoxaline-1-carboxylic acid (5-carbamoyl-adamantan-2-yl)amide;

trans 4-[5-(4-tert-Butyl-piperazin-1-yl)pyridin-2-yl]-3,4-dihydro-2H-quinoxaline-1-carboxylic acid [5-(methanesulfonylamino-methyl)adamantan-2-yl]amide;

trans 4-[5-(4-Cyclopropanesulfonyl-piperazin-1-yl)pyridin-2-yl]-3,4-dihydro-2H-quinoxaline-1-carboxylic acid (5-carbamoylmethyl-adamantan-2-yl)amide;

trans 4-[5-(4-Cyclopropanesulfonyl-piperazin-1-yl)pyridin-2-yl]-3,4-dihydro-2H-quinoxaline-1-carboxylic acid (5-aminomethyl-adamantan-2-yl)amide;

trans Carbamic acid 4-({4-[5-(4-cyclopropanesulfonyl-piperazin-1-yl)pyridin-2-yl]-3,4-dihydro-2H-quinoxaline-1-carbonyl}amino)adamantan-1-yl ester;

trans 4-[5-(4-tert-Butyl-piperazin-1-yl)pyridin-2-yl]-3,4-dihydro-2H-quinoxaline-1-carboxylic acid [5-(2,2,2-trifluoro-1-hydroxy-ethyl)adamantan-2-yl]amide;

trans 4-[5-(4-tert-Butyl-piperazin-1-yl)pyridin-2-yl]-3,4-dihydro-2H-quinoxaline-1-carboxylic acid [5-(2H-tetrazol-5-ylmethyl)adamantan-2-yl]amide;

trans 4-[5-(4-Cyclopropanesulfonyl-piperazin-1-yl)pyridin-2-yl]-3,4-dihydro-2H-quinoxaline-1-carboxylic acid (5-methoxycarbamoyl-adamantan-2-yl)amide;

trans 4-[5-(4-tert-Butyl-piperazin-1-yl)pyridin-2-yl]-3,4-dihydro-2H-quinoxaline-1-carboxylic acid (5-methanesulfonylamino-adamantan-2-yl)amide;

trans 4-[5-(4-Cyclopropanesulfonyl-piperazin-1-yl)pyridin-2-yl]-3,4-dihydro-2H-quinoxaline-1-carboxylic acid [5-(3-methyl-[1,2,4]oxadiazol-5-yl)adamantan-2-yl]amide.

It should be noted that the above compounds have been named using IUPAC nomenclature by means of the AutoNom software (Beilstein Information Systems).

Protective group (GP) means, hereinafter, a group that is able, on the one hand, to protect a reactive function such as a hydroxyl or an amine during a synthesis and, on the other hand, to regenerate the reactive function intact at the end of synthesis. Examples of protective groups as well as methods of protection and deprotection are given in "Protective Groups in Organic Synthesis", Greene et al., 3$^{rd}$ Edition (John Wiley & Sons, Inc., New York).

Leaving group (Lg, E, V, X, Z) means, hereinafter, a group that can be easily cleaved from a molecule by rupture of a heterolytic bond, with departure of an electron pair. This group can thus be replaced easily with another group during a substitution reaction, for example. Said leaving groups are, for example, halogens or an activated hydroxyl group such as a mesyl, tosyl, triflate, acetyl, paranitrophenyl, etc. Examples of leaving groups as well as methods of preparation thereof are given in "Advanced Organic Chemistry", J. March, 3$^{rd}$ Edition, Wiley Interscience, p. 310-316.

According to the invention, the compounds of general formula (I) can be prepared according to the methods presented below.

Scheme 1 (Method No. 1):

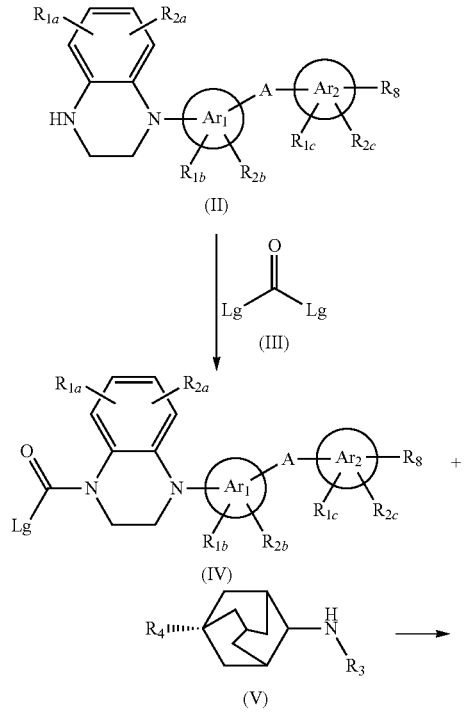

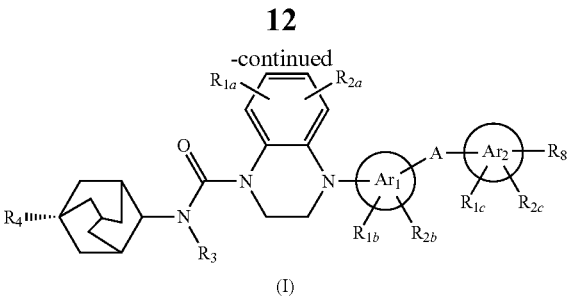

In scheme 1, the compounds of formula (IV) can be prepared by reaction between the intermediates of formula (II) and a carbonyl of formula (III) having two leaving groups Lg (for example a chlorine atom, a trichloromethoxy group, a para-nitrophenyl group, an imidazole group or methyl-imidazolium) in the presence of a base such as triethylamine or diisopropylamine, in a solvent such as dichlomethane or tetrahydrofuran and at a temperature in the range from room temperature to 80° C. The compounds of formula (I) are then obtained by coupling between the activated derivatives (IV) and the amines (V) in the presence or absence of a base such as triethylamine or potassium carbonate, in a solvent such as tetrahydrofuran, dichloromethane, acetonitrile, dimethylformamide or water, at a temperature in the range from room temperature to 100° C.

In certain cases, when $R_1$ or $R_2$ is an alcohol, or $R_1$, $R_2$ or $R_4$ is a primary or secondary amine or an acid or a bioisostere of an acid function (tetrazole, etc.) or if $Ar_1$ or $Ar_2$ has in compound (I) a secondary amine function, it is then necessary to carry out Method No. 1 with a derivative (II) or (V) where the aforementioned functions are made unreactive by the presence of a protective group (for example, for an amine: a Boc, Bn or Cbz group; for an alcohol: a Bn group; for an acid: an ester group; for a tetrazole: a benzyl group). Finally, to obtain the desired functionality, it is then necessary to carry out a reaction of deprotection in conditions known by a person skilled in the art.

The heterocycles of general formula (V) are available commercially or can be prepared by methods described in the literature (for example WO 2007/077949, US 2005/0215784 A1, US 2005/0245745 A1, Journal of Organic Chemistry (2005), 70(20), 7919-7924).

Scheme 2 gives the details of a synthesis of the compounds of formula (I) in which $R_4$ represents an aminoalkyl function; these compounds will be called compounds of formula (VI) hereinafter.

Scheme 2 (Method No. 2):

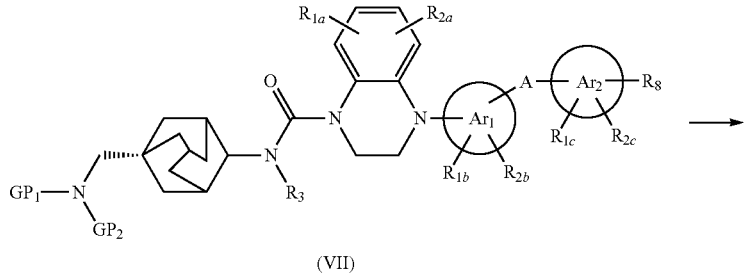

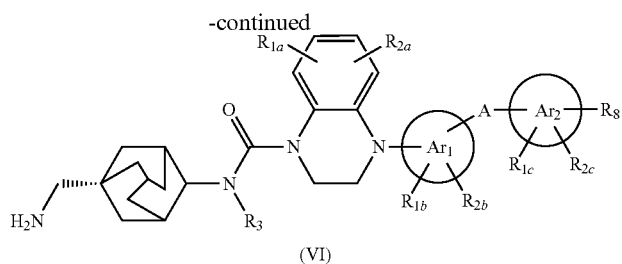

(VI)

In scheme 2, the compounds (VII) have an aminoalkyl function protected by means of two protective groups (GP$_1$ and GP$_2$). The compounds (VI) are obtained by deprotection of the amine function of the compounds of formula (VII), for example if GP$_1$ and/or GP$_2$ is a benzyl or carboxybenzyl group, the possible methods of deprotection comprise, among others, the use of hydrogen in the presence of a catalyst derived from palladium for performing a reaction of hydrogenolysis, in a solvent or mixture of solvents such as methanol, ethanol, ethyl acetate, tetrahydrofuran, under a hydrogen pressure between 1 and 10 bar at a temperature in the range from room temperature to 80° C. An alternative method for performing a hydrogenolysis of the benzyl or carboxybenzyl protective group consists of using a palladium catalyst (for example with palladium adsorbed on charcoal) in the presence of ammonium formate under reflux of a solvent such as methanol.

Scheme 3 gives the details of a synthesis of the compounds of formula (I) in which R$_4$ represents a hydroxy-alkyl group substituted with a haloalkyl; these compounds will be called compounds of formula (VIII) hereinafter.

In scheme 3, the derivatives (X) are obtained by reduction of the ester function of the compound (IX) to an alcohol function by means of a hydride such as LiAlH$_4$, LiBH$_4$, DiBal in a solvent or mixture of solvents such as tetrahydrofuran, ether or toluene, at a temperature in the range from −78° C. to 40° C. The next step consists of oxidizing the alcohol function of the derivatives (X) to an aldehyde function to obtain the compounds (XI), using an oxidant such as the Dess-Martin reagent, PCC or Tpap in the presence or absence of a co-oxidant such as N-methylmorpholine N-oxide for example, in a solvent such as dichloromethane, dichloroethane generally at room temperature. A Swern oxidation reaction as described in Synthesis 1990, pp 857-870 can also lead to the same compounds (XI). Finally, the derivatives (VIII) are obtained by addition of a haloalkyl group, for example a trifluoromethyl group on the aldehyde function of the compounds (XI) by means of the Ruppert reagent or equivalent in the presence or absence of a source of fluoride ion such as TBAF or CsF in a solvent such as THF or DMF at a temperature between −25° C. and room temperature.

Scheme 3 (Method No. 3):

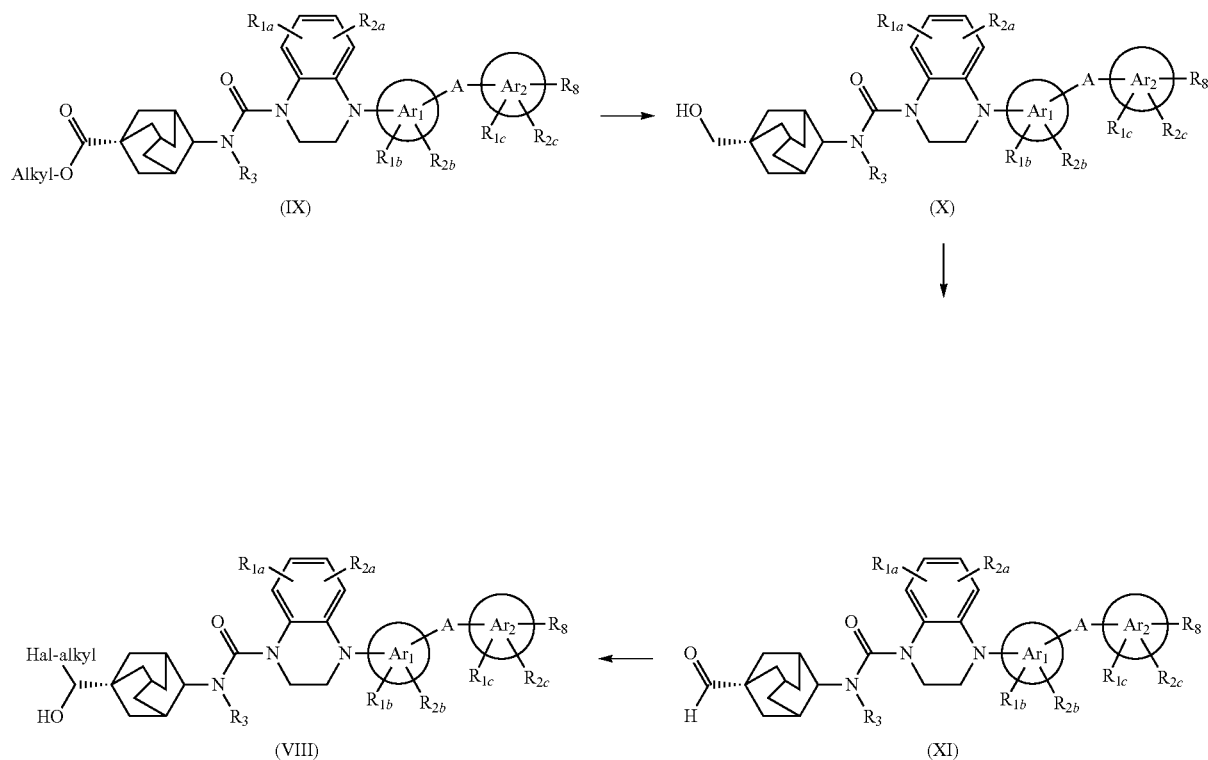

Scheme 4 gives the details of a synthesis of the compounds of formula (I) in which $R_4$ represents a carbamate function; these compounds will be called compounds of formula (XII) hereinafter.

Scheme 4 (Method No. 4):

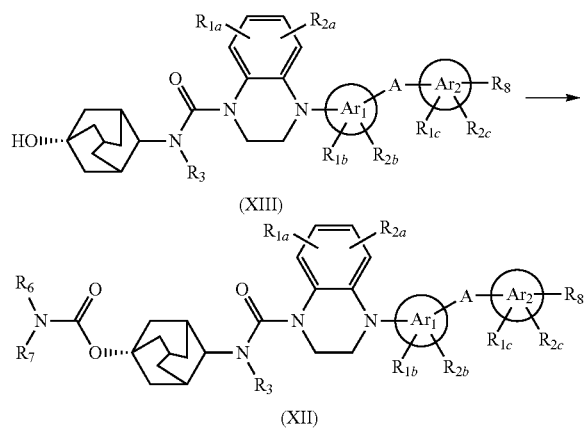

In scheme 4, the derivatives (XII) are obtained by a coupling reaction between the alcohol function of the derivative (XIII) and an isocyanate or a carbamoyl chloride in the presence or absence of a base such as triethylamine or potassium carbonate, in a solvent such as tetrahydrofuran, dichloromethane, acetonitrile, dimethylformamide or water, at a temperature in the range from room temperature to 100° C. In the particular case when $R_6$ and $R_7$ are two hydrogens, the reagent used can be trichloroacetylisocyanate and it is then necessary to withdraw the protection on the nitrogen atom by basic hydrolysis with for example $K_2CO_3$ as base, in a solvent such as methanol and at a temperature between room temperature and 50° C.

Scheme 5 gives the details of a synthesis of the compounds of formula (V) in which $R_3$ is a hydrogen and $R_4$ is an alkylsulfonamide group; these compounds will be called compounds of formula (XIV) hereinafter.

In scheme 5, the derivatives (XVI) are obtained by protection of the amine function of the derivative (XV), for example with a Boc group by methods that are known by a person skilled in the art. In a second step, the acid function of the derivatives (XVI) undergoes a Curtius reaction such as described for example with adamantane derivatives by Maison et al., in J. Org. Chem. 2008, pp 1056 or by Broadhurst et al., in J. Med. Chem. 2004, pp 4975. The amines (XVIII) are obtained by deprotection of the carbamate function of the compounds of formula (XVII) by methods selected from those known by a person skilled in the art. The possible methods of deprotection comprise among other things the use of hydrogen in the presence of a catalyst derived from palladium for performing a reaction of hydrogenolysis, in a solvent or mixture of solvents such as methanol, ethanol, ethyl acetate, tetrahydrofuran, under a hydrogen pressure between 1 and 10 bar at a temperature in the range from room temperature to 80° C. An alternative method for performing hydrogenolysis of the Cbz group consists of using palladium catalysis (for example with palladium adsorbed on charcoal) in the presence of ammonium formate under reflux of a solvent such as methanol. In the next step, the compounds (XVIII) are reacted with a sulfonyl chloride in the presence of a base such as triethylamine or pyridine in a solvent such as dichloromethane, chloroform or THF at a temperature between −10° C. and 50° C. The amines (XIV) are obtained by deprotection of the amine function of the compounds of formula (XIX), by methods selected from those known by a person skilled in the art; they comprise among others the use of trifluoroacetic acid or hydrochloric acid in dichloromethane, dioxane, tetrahydrofuran or diethyl ether in the case of protection by a Boc group, and of piperidine for an Fmoc group, at temperatures in the range from −10 to 100° C.

Scheme 6 gives the details of a synthesis of the compounds of formula (V) in which $R_3$ is a hydrogen and $R_4$ an alkylsulfonamide-alkyl group; these compounds will be called compounds of formula (XX) hereinafter.

Scheme 5

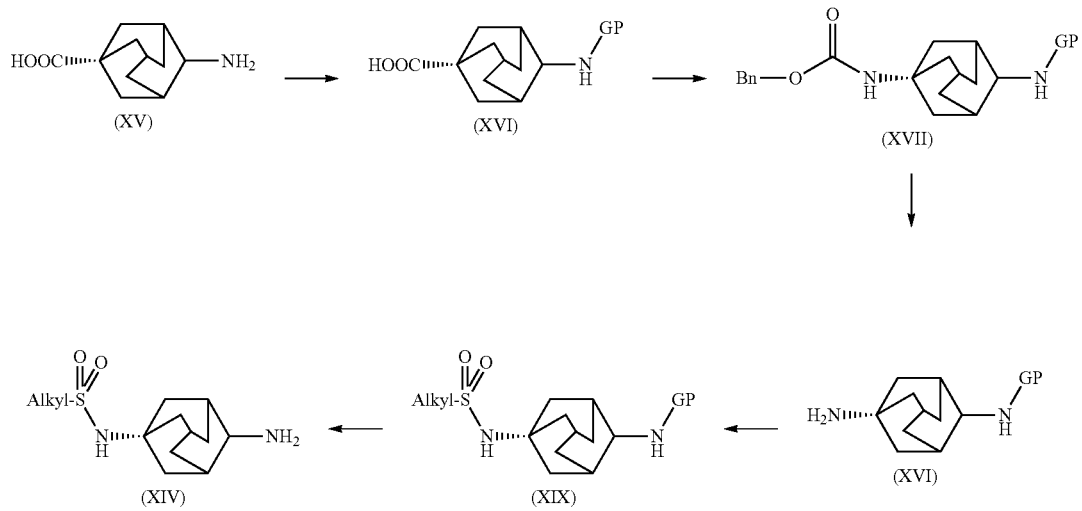

Scheme 6:

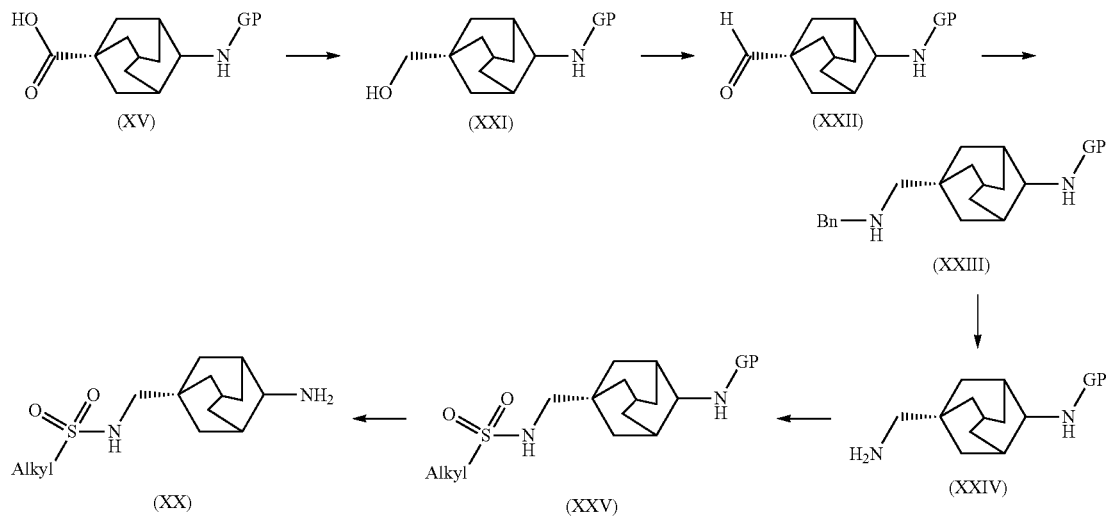

In scheme 6, the derivatives (XXI) are obtained by reduction of the acid function of the compound (XV) to an alcohol function by means of a hydride such as LiAlH$_4$, BH$_3$, THF in a solvent or mixture of solvents such as tetrahydrofuran, ether or toluene, at a temperature in the range from −78° C. to 40° C. The next step consists of oxidizing the alcohol function of the derivatives (XXI) to an aldehyde function to obtain the compounds (XXII), using an oxidant such as the Dess-Martin reagent, PCC or Tpap in the presence or absence of a co-oxidant such as N-methylmorpholine N-oxide for example, in a solvent such as dichloromethane, dichloroethane generally at room temperature. A Swern oxidation reaction as described in Synthesis 1990, pp 857-870 can also lead to the same compounds (XXII). The aldehyde function of the derivative (XXII) is transformed to an amine group to obtain the compounds (XXIII) by a reaction of reductive amination with an amine such as benzylamine using a reducing agent such as sodium borohydride, sodium triacetoxyborohydride or sodium cyanoborohydride, in the presence or absence of a Brønsted acid (such as hydrochloric acid) or a Lewis acid (such as titanium tetraisopropoxide) in a solvent such as dichloroethane, dichloromethane, acetic acid or methanol, at temperatures between −10° C. and 30° C. The derivatives (XXIV) are then obtained by deprotection of the benzyl function carried on the aminomethyl group of the compounds (XXIII). The possible methods of deprotection comprise among others the use of hydrogen in the presence of a catalyst derived from palladium for performing a reaction of hydrogenolysis, in a solvent or mixture of solvents such as methanol, ethanol, ethyl acetate, tetrahydrofuran, under a hydrogen pressure between 1 and 10 bar at a temperature in the range from room temperature to 80° C. An alternative method for performing hydrogenolysis of the Bn group consists of using palladium catalysis (for example with palladium adsorbed on charcoal) in the presence of ammonium formate under reflux of a solvent such as methanol. In the next step, for obtaining the derivatives sulfonamides (XXV), the compounds (XXIV) are reacted with a sulfonyl chloride in the presence of a base such as triethylamine or pyridine in a solvent such as dichloromethane, chloroform or THF at a temperature between −10° C. and 50° C. The amines (XX) are obtained by deprotection of the amine function of the compounds of formula (XXV) by methods selected from those known by a person skilled in the art; they comprise among others the use of trifluoroacetic acid or hydrochloric acid in dichloromethane, dioxane, tetrahydrofuran or diethyl ether in the case of protection by a Doc group, and of piperidine for an Fmoc group, at temperatures in the range from −10 to 100° C.

Scheme 7 gives the details of a synthesis of the compounds of formula (V) in which R$_3$ is a hydrogen and R$_4$ an alkylamide group; these compounds will be called hereinafter compounds of formula (XXVI).

Scheme 7:

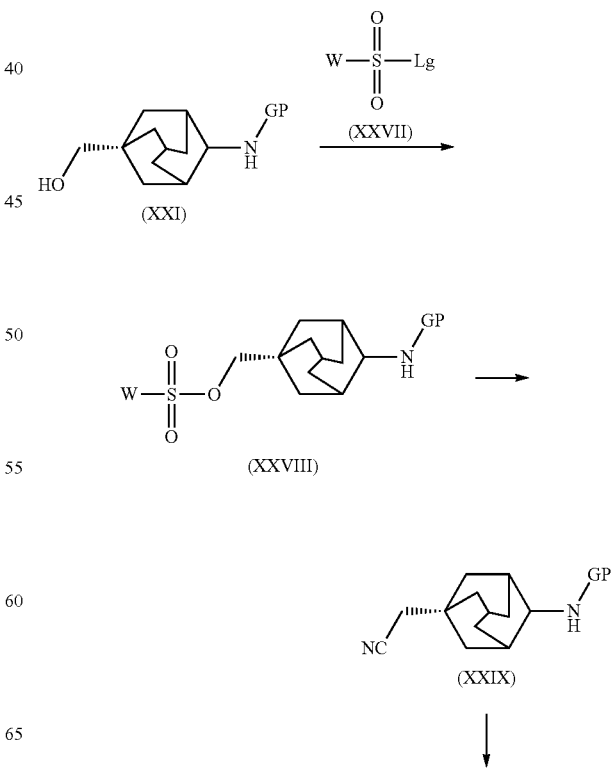

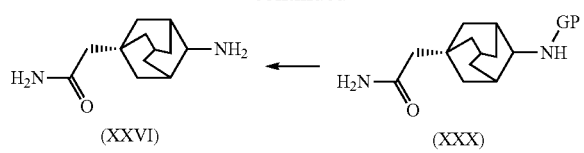

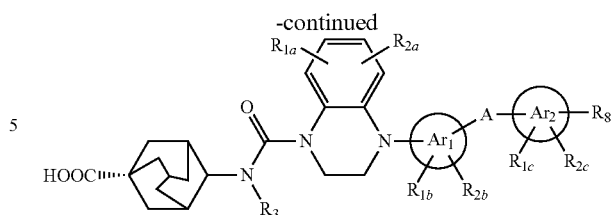

In scheme 7, the alcohol function of the derivatives (XXI) is transformed to a sulfonic ester to form the compounds of formula (XXVIII) by the action of a sulfonic derivative (XXVII) in which $WSO_2$ represents for example a tosylate, triflate or nanoflate group, such as a sulfonic anhydride ($Lg=OSO_2W$), a sulfonic acid fluoride ($Lg=F$) or a sulfonic acid chloride ($Lg=Cl$), in the presence of a base or of a mixture of bases such as triethylamine, pyridine, dimethylaminopyridine, diisopropylethylamine or potassium carbonate in a solvent or mixture of solvents such as dichloromethane, chloroform, toluene, tetrahydrofuran, dimethylformamide or acetonitrile, at a temperature in the range from −78° C. to 100° C. In the next step, the sulfonic ester of the derivatives (XXVIII) is substituted with a cyano group, leading to the compounds (XXIX), using a cyanide such as KCN or NaCN in a solvent such as DMF or DMSO, at a temperature between room temperature and 150° C. Then the cyano function of the derivatives (XXIX) is transformed to a primary amide group to obtain the compounds (XXX) by acid hydrolysis for example using sulfuric acid in the absence or presence of a solvent such as water, at a temperature between room temperature and 100° C. Finally, in the last step, the amines (XXVI) are obtained by deprotection of the amine function of the compounds of formula (XXX), by methods selected from those known by a person skilled in the art; they comprise among others the use of piperidine for an Fmoc group at temperatures in the range from −10 to 100° C. In the case of protection by a Boc group, the product (XXVI) is generally obtained directly from the compounds (XXIX) in acid hydrolysis of the cyano function.

Scheme 8 gives the details of a synthesis of the compounds of formula (I) in which $R_4$ represents an amide function; these compounds will be called compounds of formula (XXXI) hereinafter.

Scheme 8 (Method No. 5):

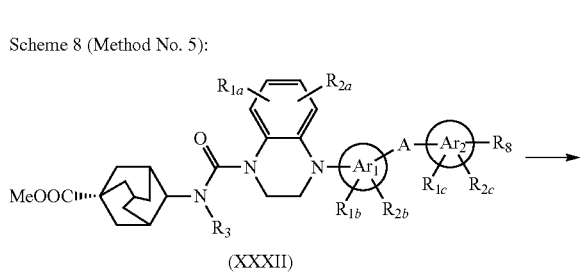

In scheme 8, the ester function of the compound (XXXII) is saponified to an acid function using sodium, potassium or lithium hydroxide in a solvent or mixture of solvents such as an alcohol, water or tetrahydrofuran, at a temperature in the range from room temperature to 100° C., leading to the acid (XXXIII). In the last step, the compound (XXXI) can be prepared by condensation between the acid intermediate of formula (XXXIII) and an amine (XXXIV) in classical conditions of peptide coupling, using for example dicyclocarbodiimide, 1-(3-dimethylaminopropyl)-3-ethylcarbodiimide hydrochloride or bromo-tris-pyrrolidino-phosphonium hexafluorophosphate as coupling agent, in the presence or absence of hydroxybenzotriazole, and using triethylamine or diisopropyl-ethylamine as organic base in a solvent or mixture of solvents such as dioxane, dichloromethane or acetonitrile.

Scheme 9 gives the details of, a synthesis of the compounds of formula (II).

Scheme 9:

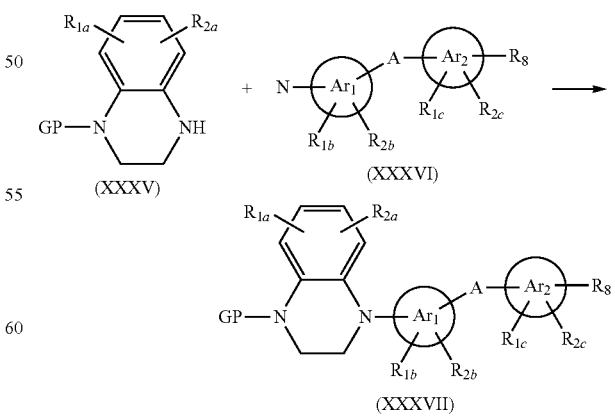

-continued

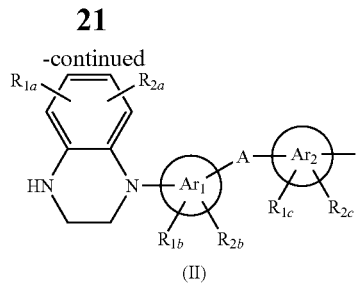

(II)

Scheme 10:

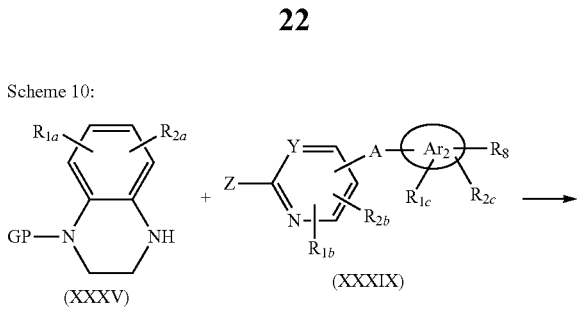

In scheme 9, the compounds of formula (XXXVII) can be prepared by coupling between a monoprotected tetrahydroquinoxaline of formula (XXXV) and a derivative (XXXVI) having a leaving group X (for example a halogen, a tosylate, triflate or nanoflate group) in the presence of an organometallic catalyst such as a derivative of palladium, in the presence or absence of a phosphine such as tritertbutylphosphine or triphenylphosphine, in the presence of a base such as potassium carbonate, potassium fluoride, potassium tertbutylate or potassium phosphate in a solvent or mixture of solvents such as dioxane, ethylene glycol dimethyl ether, toluene, tetrahydrofuran or water, at a temperature in the range from room temperature to 100° C. The amines (II) are obtained by deprotection of the amine function of the compounds of formula (XXXVII), by methods selected from those known by a person skilled in the art; they comprise among others the use of trifluoroacetic acid or hydrochloric acid in dichloromethane, dioxane, tetrahydrofuran or diethyl ether in the case of protection by a Boc group, and of piperidine for an Fmoc group, at temperatures in the range from −10 to 100° C.

The heterocycles of general formula (XXXV) are available commercially or can be prepared by methods described in the literature (for example "Comprehensive heterocyclic chemistry", Katritzky et al., 2$^{nd}$ Edition (Pergamon Press); Krchnak, V. et al., Tet. Lett (2001), 42, 2443-2446; Eary, C. T. et al., Tet. Lett. (2006), 47, 6899-6902; Savrides, E-M. et al., J. Het. Chem. (2005), 42, 1031-1034; De Selms, R. C. et al., J. Het. Chem. (1974), 11(4), 595-7.

The compounds of general formula (XXXVI) are available commercially or can be prepared by methods described in the literature (for example Z. Sui et al., Bioorg. Med. Chem. Lett. (2003), 13, 761-765; Chopa, A. B. et al., J. Organomet. Chem. (2005), 690(17), 3865-3877; Düaggeli, M. et al., Org. Biomol. Chem. (2003), 1(11), 1894-1899; Gros, P. et al., J. Org. Chem. (2003), 68(5), 2028-2029; Bouillon, A. et al., Tet. (2002), 58(14), 2885-2890; Balle, T. et al., J. Med. Chem. (2006), 49(11), 3159-3171; M. A. Ismail et al., J. Med. Chem. (2006), 49(17), 5324-5332, Gu, Y. G. et al., J. Med. Chem. (2006), 49(13), 3770-3773; Serafin, B. et al., Eur. J. Med. Chem. (1977), 12(4), 325-31; Schmidt, H.-W. et al., J. Het. Chem. (1987), 24(5), 1305-7; Walsh, D. A. et al., J. Med. Chem. (1990), 33(7), 2028-32; WO 2005/042521; EP 0 277 725).

Scheme 10 gives the details of a synthesis of the compounds of formula (XXXVII) in which $Ar_1$ represents a pyridine nucleus (Y=C) or pyrimidine nucleus (Y=N); these compounds will be called compounds of formula (XXXVIII) hereinafter.

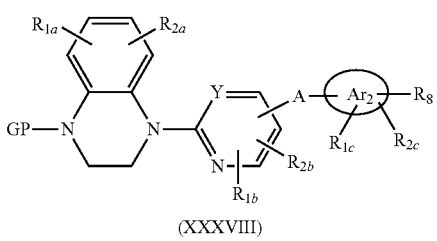

(XXXVIII)

In scheme 10, the compounds of formula (XXXVIII) can be prepared by a reaction of aromatic nucleophilic substitution between a monoprotected tetrahydroquinoxaline of formula (XXXV) and a derivative (XXXIX) having a leaving group Z (for example a halogen or an alkylsulfonyl group) in the presence of a base such as the lithium salt of hexamethyldisilazane or sodium hydride in a solvent such as tetrahydrofuran, N-methylpyrrolidinone, dimethylsulfoxide or dimethylformamide, at a temperature in the range from room temperature to 100° C.

Scheme 11 gives the details of a synthesis of the compounds of formula (XXXVII) in which $Ar_1$ represents a phenyl nucleus and A represents a bond; these compounds will be called compounds of formula (XXXX) hereinafter.

Scheme 11:

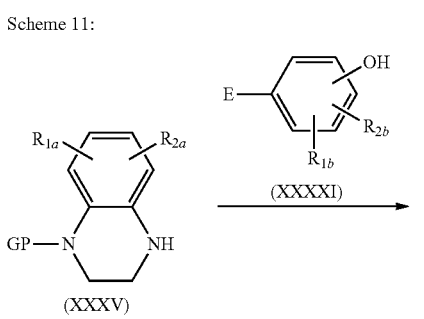

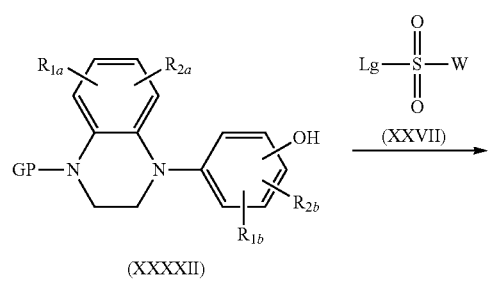

(XXXXII)

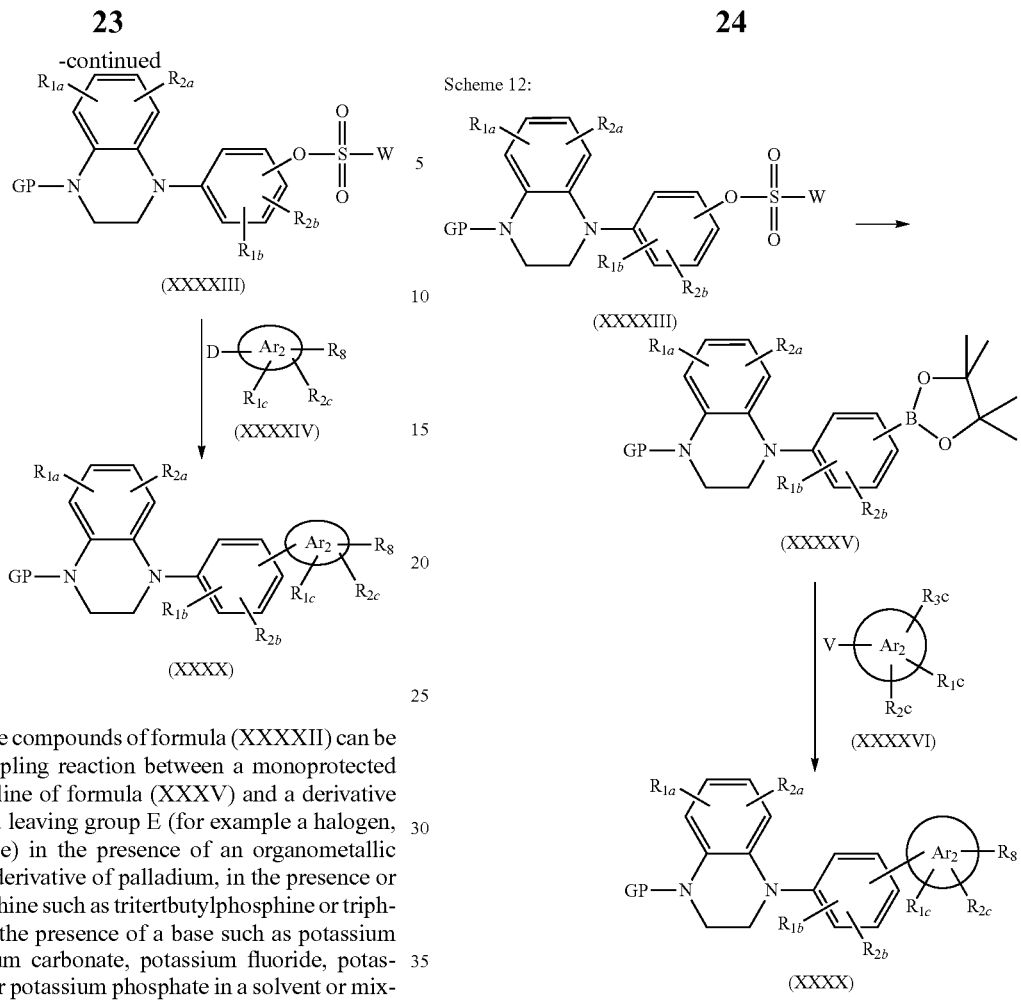

In scheme 11, the compounds of formula (XXXXII) can be prepared by a coupling reaction between a monoprotected tetrahydroquinoxaline of formula (XXXV) and a derivative (XXXXI) having a leaving group E (for example a halogen, triflate or nanoflate) in the presence of an organometallic catalyst such as a derivative of palladium, in the presence or absence of a phosphine such as tritertbutylphosphine or triphenylphosphine, in the presence of a base such as potassium carbonate or cesium carbonate, potassium fluoride, potassium tertbutylate or potassium phosphate in a solvent or mixture of solvents such as dioxane, ethylene glycol dimethyl ether, toluene, tetrahydrofuran or water, at a temperature in the range from room temperature to 100° C. The phenol function is then transformed to a sulfonic ester to form the compounds of formula (XXXXIII) by the action of a sulfonic derivative (XXVII) where $WSO_2$ represents for example a tosylate, triflate or nanoflate group, such as a sulfonic anhydride (Lg=$OSO_2W$), a sulfonic acid fluoride (Lg=F) or a sulfonic acid chloride (Lg=Cl), in the presence of a base or of a mixture of bases such as triethylamine, pyridine, dimethylaminopyridine, diisopropylethylamine or potassium carbonate in a solvent or mixture of solvents such as dichloromethane, chloroform, toluene, tetrahydrofuran, dimethylformamide or acetonitrile, at a temperature in the range from −78° C. to 100° C. Finally, the derivatives (XXXX) can be obtained by a coupling reaction between a derivative (XXXXIII) and a compound (XXXXIV) in which D is either an organometallic group D (for example a derivative of boron, a derivative of tin or an organozinc compound) or a hydrogen atom when it is bound directly to the nitrogen atom of an amine of a heterocycloalkyl, in the presence of an organometallic species such as a derivative of palladium, in the presence or absence of a phosphine such as tricyclohexylphosphine or triphenylphosphine, in the presence of a base such as potassium carbonate or potassium fluoride in a solvent or mixture of solvents such as dioxane, dimethylformamide, ethylene glycol dimethyl ether, tetrahydrofuran or water, at a temperature in the range from room temperature to 100° C.

Scheme 12 presents an alternative synthesis of the compounds of formula (XXXX).

In scheme 12, the compounds of formula (XXXXV) can be prepared by transformation of the sulfonic ester function of compound (XXXXIII) to a boronic ester function to obtain the compounds of formula (XXXXV) by a reaction with bispinacolatodiborane in the presence of a complex of palladium such as 1,1'-bis(diphenylphosphino)ferrocedichloropalladium (II) in the presence of a base such as potassium acetate and lithium chloride in a solvent or mixture of solvents such as dichloromethane, dioxane or dimethylsulfoxide, at a temperature in the range from room temperature to 100° C. In a second step, the derivatives (XXXX) can be obtained by a coupling reaction between the derivative (XXXXV) and a compound (XXXXVI) having a leaving group V (for example a halogen, a triflate, a nonaflate) in the presence of an organometallic catalyst such as a derivative of palladium, in the presence or absence of a phosphine such as tricyclohexylphosphine or triphenylphosphine, in the presence of a base such as sodium carbonate or potassium carbonate or potassium fluoride, in a solvent or mixture of solvents such as dioxane, dimethylformamide, ethylene glycol dimethyl ether, tetrahydrofuran or water, at a temperature in the range from room temperature to 100° C.

Scheme 13 gives the details of a synthesis of the compounds of formula (XXXVII) in which $Ar_1$ represents a pyridine nucleus (just one of the two atoms Y is a nitrogen, the other is a carbon) and A represents a bond; these compounds will be called compounds of formula (XXXXVII) hereinafter.

Scheme 13:

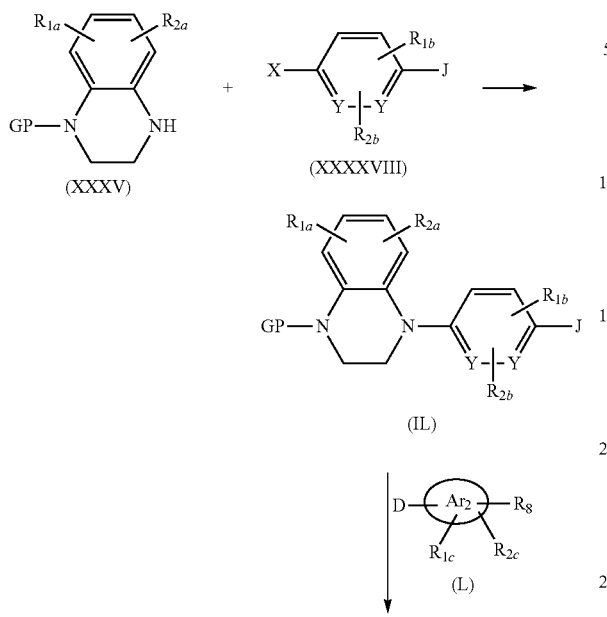

of formula (XXXV) and a derivative (XXXXVIII) having a leaving group X (for example a fluorine atom) and a leaving group J (for example a bromine atom) in the presence of a base such as potassium tertbutylate or sodium hydride in a solvent such as N-methylpyrrolidinone or dimethylformamide, at a temperature in the range from room temperature to 100° C. Finally, the derivatives (XXXXVII) can be obtained by a coupling reaction between a derivative (IL) and a compound (L) in which D is either an organometallic group (for example a derivative of boron, a derivative of tin or an organozinc compound) or a hydrogen atom when it is bound directly to the nitrogen atom of an amine of a heterocycloalkyl, in the presence of an organometallic catalyst such as a derivative of palladium, in the presence or absence of a phosphine such as tricyclohexylphosphine or triphenylphosphine, in the presence of a base such as potassium carbonate or cesium carbonate, potassium triphosphate, sodium tertbutylate or potassium tertbutylate or potassium fluoride, in a solvent or mixture of solvents such as toluene, dioxane, dimethylformamide, ethylene glycol dimethyl ether, tetrahydrofuran or water, at a temperature in the range from room temperature to 100° C.

Scheme 14 gives the details of a synthesis of the compounds of formula (I) in which $R_4$ represents a 1,2,4-oxadiazole group substituted with an alkyl; these compounds will be called compounds of formula (LI) hereinafter.

Scheme 14 (Method No. 6):

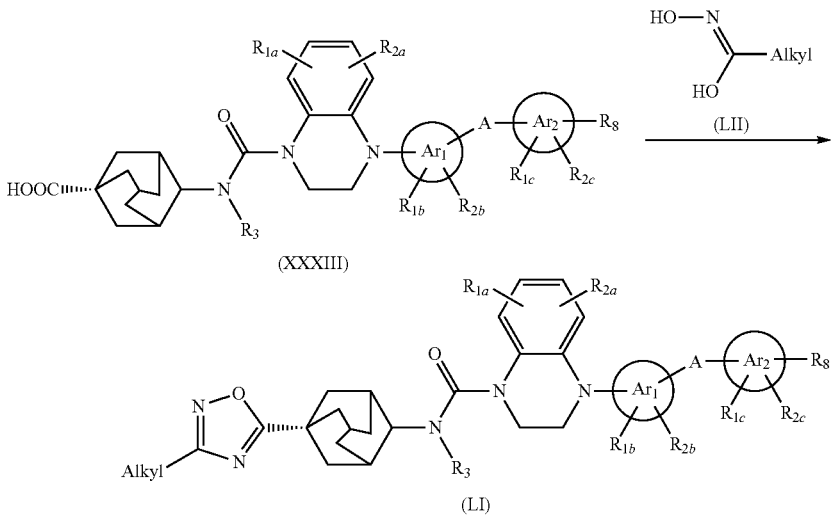

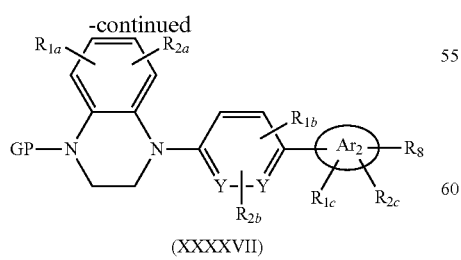

In scheme 13, the compounds of formula (IL) can be prepared by a reaction of aliphatic or aromatic nucleophilic substitution between a monoprotected tetrahydroquinoxaline In scheme 14, the compounds (LI) are obtained by reaction of the acids (XXXIII) with the hydroxyamidine derivatives (LII) in the presence of a coupling agent such as O-benzotriazol-1-yl-N,N,N',N'-tetramethyluronium tetrafluoroborate, DIC, DCC or EDC, in the presence or absence of 1-hydroxybenzotriazole, of a base such as triethylamine, diisopropylethylamine in a solvent such as dimethylformamide, tetrahydrofuran or acetonitrile at a temperature varying between room temperature and 100° C. If the cyclization reaction is not obtained, it may be necessary to perform an additional step of cyclizing dehydration in the presence of sodium acetate.

Scheme 15 gives the details of a synthesis of the compounds of formula (I) in which $R_4$ represents an alkoxy-imino group; these compounds will be called compounds of formula (LIII) hereinafter.

Scheme 15 (Method No. 7):

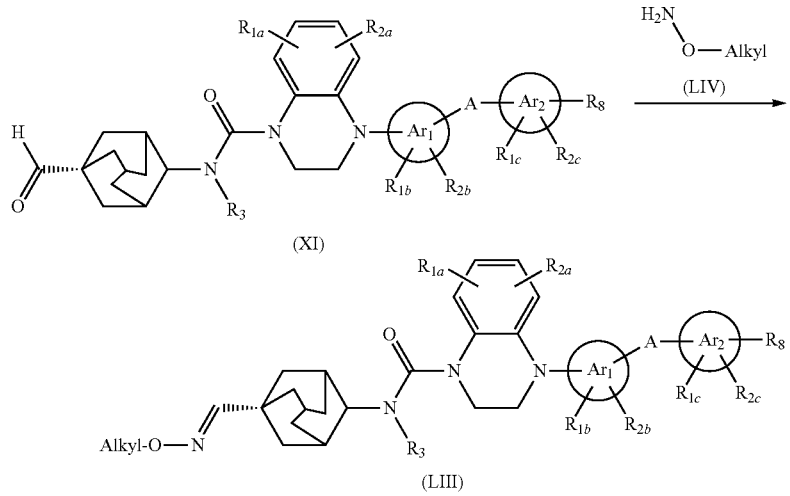

(XI)

(LIII)

In scheme 15, the oximes (LIII) are obtained by transformation of the aldehyde function of the compounds (XI) by means of O-alkyl-hydroxyamine in the form of base or of hydrochloride in the presence of or absence of a base such as sodium acetate or triethylamine in a solvent such as methanol or ethanol at a temperature in the range from 0° C. to room temperature.

Scheme 16 gives the details of a synthesis of the compounds of formula (V) in which $R_3$ is a hydrogen and $R_4$ is a group —O-alkyl-CO—$NR_6R_7$; these compounds will be called compounds of formula (LV) hereinafter.

Scheme 16:

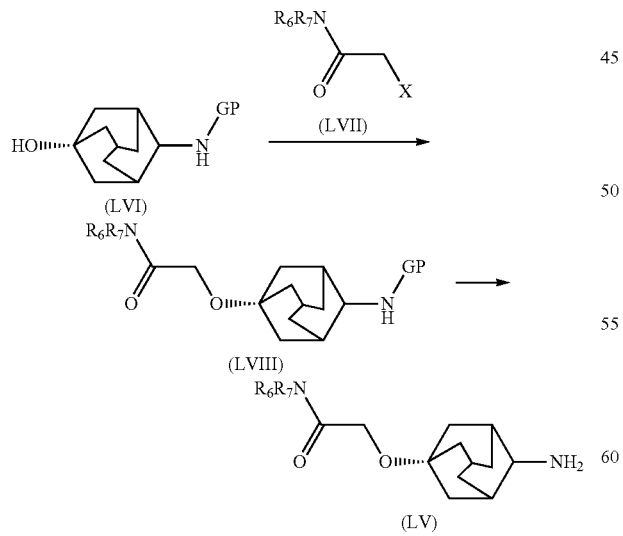

In scheme 16, the alcohol function of the derivatives (LVI) is transformed to a group —O-alkyl-CO—$NR_6R_7$ (LVIII) by the action of an alkylamide derivative (LVII), where X represents a leaving group, for example a bromine or chlorine atom, a tosylate, triflate or nanoflate group, in the presence of a base or a mixture of bases such as sodium hydride, sodium tert-butylate or potassium tert-butylate in a solvent or mixture of solvents such as tetrahydrofuran or dimethylformamide, at a temperature in the range from –78° C. to 100° C. Finally, in the next step, the amines (LV) are obtained by deprotection of the amine function of the compounds of formula (LVIII), by methods selected from those known by a person skilled in the art; they comprise among others the use of trifluoroacetic acid or hydrochloric acid in dichloromethane, dioxane, tetrahydrofuran or diethyl ether in the case of protection by a Boc group, and of piperidine for an Fmoc group, at temperatures in the range from –10 to 100° C.

Scheme 17 gives the details of a synthesis of the compounds of formula (V) in which $R_3$ is a hydrogen and $R_4$ is a group —O—$SO_2$—$NR_6R_7$; these compounds will be called compounds of formula (LIX) hereinafter.

Scheme 17:

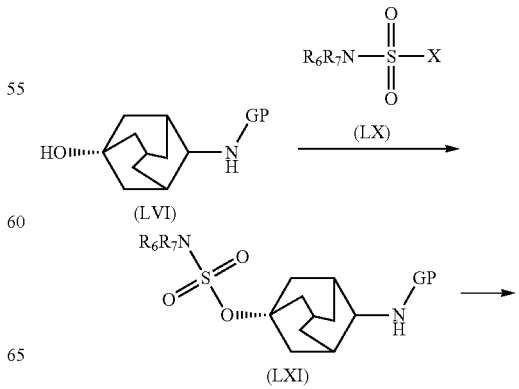

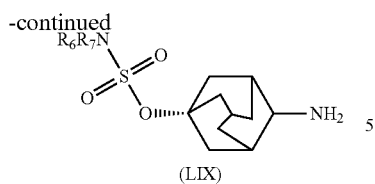

(LIX)

In scheme 17, the derivatives (LXI) are obtained by a coupling reaction between the alcohol function of the derivative (LVI) and a sulfamoyl chloride or bromide in the presence or absence of a base such as triethylamine or potassium carbonate, in a solvent such as dimethylformamide, toluene or hexane at a temperature in the range from room temperature to 100° C. Finally, in the next step, the amines (LIX) are obtained by deprotection of the amine function of the compounds of formula (LXI), by methods selected from those known by a person skilled in the art; they comprise among others the use of trifluoroacetic acid or hydrochloric acid in dichloromethane, dioxane, tetrahydrofuran or diethyl ether in the case of protection by a Boc group, and of piperidine for an Fmoc group, at temperatures in the range from −10 to 100° C.

In the schemes presented above, the starting compounds and the reagents, when their manner of preparation is not described, are commercially available or are described in the literature, or else can be prepared according to methods that are described in the literature or that are known by a person skilled in the art.

According to another of its aspects, the invention also relates to the compounds of formulas (II), (IV), (VII), (IX), (X), (XI), (XIII), (XXXII), (XXXIII), (XXXV), (XXXVI), (XXXVII), (XXXVIII), (XXXX), (XXXXIII), (XXXXV), (XXXXVII), (LV), (LIX) defined above. These compounds are useful as intermediates for synthesis of the compounds of formula (I).

The following examples describe the preparation of some compounds according to the invention. These examples are not limiting and are only intended to illustrate the present invention. The numbers of the compounds in the examples refer to those given in the table hereunder, which illustrates the chemical structures and the physical properties of some compounds according to the invention.

The following abbreviations, usual reagents and empirical formulas are used:

BoC tert-butyloxycarbonyl
° C. degree Celsius
Cbz carboxybenzyl
CsF cesium fluoride
DCC dicyclohexylcarbodiimide
DiBal diisobutylaluminum
DIC diisopropylcarbodiimide
DME dimethoxyethane
DMF dimethylformamide
DMSO dimethyl sulfoxide
EDC 1-ethyl-3-(3-dimethylaminopropyl)-carbodiimide
Fmoc fluorenylmethoxycarbonyl
h hour(s)
$H_2$ dihydrogen
$H_2O$ water
HCl hydrochloric acid
Hobt hydroxybenzotriazole
$K_2CO_3$ potassium carbonate
LC/MS liquid chromatography/mass spectrometry
ml or mL milliliter(s)
mmol millimole(s)
MHz megahertz
$MgSO_4$ magnesium sulfate
N normal
NMP N-methylmorpholine
$NaHCO_3$ sodium hydrogen carbonate
PCC pyridinium chlorochromate
Pd/C palladium on charcoal
$P_2O_5$ phosphorus pentoxide
ppm parts per million
psi pounds per square inch
Dess-Martin reagent (1,1,1-triacetoxy)-1,1-dihydro-1,2-benziodoxol-3(1H)-one
Ruppert reagent (trifluoromethyl)trimethylsilane
$SO_2$ sulfur dioxide
TBAF tetrabutylammonium fluoride
Tpap tetrapropylammonium perruthenate
S-Phos 2-dicyclohexylphosphino-2',6'-dimethoxybiphenyl
$Pd_2(dba)_3$ tris(dibenzylideneacetone)dipalladium (0)

Example 1

Trans [5-(Methanesulfonylamino-methyl)adamantan-2-yl]amide 4-[5-(4-tert-butyl-piperazin-1-yl)pyridin-2-yl]-3,4-dihydro-2H-quinoxaline-1-carboxylic acid (compound No. 2)

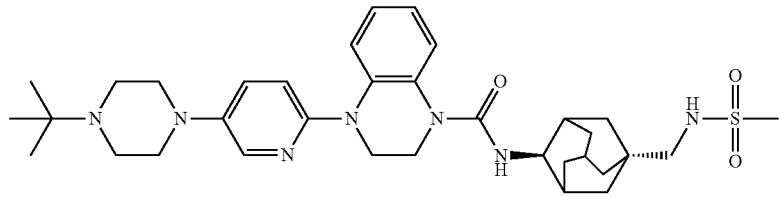 [SMILES: CC(C)(C)N1CCN(c2ccc(N3CCN(C(=O)N[C@H]4C5CC6CC4C[C@@](CNS(C)(=O)=O)(C6)C5)c4ccccc43)nc2)CC1]

1.1: Trans tert-butyl ester of (5-hydroxymethyl-adamantan-2-yl)-carbamic acid

In a three-necked flask under nitrogen, 0.5 g of trans 4-tert-butoxycarbonylamino-adamantane-1-carboxylic acid is dissolved in 8.5 ml of anhydrous tetrahydrofuran. The solution is cooled to 0° C. 5.1 ml of a 1-molar solution of borane tetrahydrofuran complex is added dropwise. It is stirred for 2 h at room temperature, then the reaction mixture is hydrolyzed gently with a few drops of water. A saturated aqueous solution of potassium hydrogen sulfate is added to pH 1 and the reaction mixture is extracted with ethyl acetate until exhaustion of the aqueous phase. The organic phases are combined, washed with water and then with a saturated aqueous solution of sodium chloride, dried over magnesium sulfate and concentrated to dryness. 0.58 g of trans tert-butyl ester of (5-hydroxymethyl-adamantan-2-yl)-carbamic acid is obtained, and is used subsequently as it is.

M+H$^+$=282

1.2: Trans tert-butyl ester of (5-formyl-adamantan-2-yl)-carbamic acid

In a three-necked flask under nitrogen, 0.45 g of trans tert-butyl ester of (5-hydroxymethyl-adamantan-2-yl)-carbamic acid is dissolved in 16 ml of anhydrous dichloromethane. The solution is cooled to 0° C. 0.75 g of 4-angstrom molecular sieve is added, and then 0.28 g of 4-methylmorpholine N-oxide and 0.028 g of tetrapropylammonium perruthenate. It is stirred for 4 h at room temperature. The reaction mixture is filtered on a mixture composed of 5 g of silica and 5 g of diatomaceous silica, rinsing with dichloromethane. The filtrate is concentrated to dryness. 0.3 g of trans tert-butyl ester of (5-formyl-adamantan-2-yl)-carbamic acid is obtained, and is used subsequently as it is.
M+H$^+$=280

1.3: Trans tert-butyl ester of [5-(benzylamino-methyl)adamantan-2-yl]-carbamic acid In a three-necked flask under nitrogen, 0.2 g of trans tert-butyl ester of (5-formyl-adamantan-2-yl)-carbamic acid is dissolved in 7 ml of anhydrous dichloromethane. 0.084 g of benzylamine, 0.2 g of 4-angstrom molecular sieve are added, and then 0.23 g of sodium triacetoxyborohydride. It is stirred overnight at room temperature. A 1N aqueous solution of hydrochloric acid is added and it is washed once with diethyl ether. The aqueous phase is basified with 5N aqueous soda solution and then extracted with dichloromethane until exhaustion of the aqueous phase. The organic phases are combined, washed with water and then with a saturated aqueous solution of sodium chloride, dried over magnesium sulfate and concentrated to dryness. 0.27 g of trans tert-butyl ester of [5-(benzylamino-methyl)adamantan-2-yl]-carbamic acid is obtained, and is used subsequently as it is.
M+H$^+$=371

1.4: Trans tert-butyl ester of (5-aminomethyl-adamantan-2-yl)-carbamic acid

In a three-necked flask under nitrogen, 0.26 g of trans tert-butyl ester of [5-(benzylamino-methyl)adamantan-2-yl]-carbamic acid is dissolved in 7 ml of methanol. 0.062 g of 10% palladium on charcoal, wetted to 50% with water, is added, and then 0.45 g of ammonium formate. It is heated under reflux for 1 hour 30 minutes. The reaction mixture is filtered on a paper filter. The solution is concentrated to dryness. The residue is taken up in 1N aqueous soda solution. It is extracted with ethyl acetate until exhaustion of the aqueous phase. The organic phases are combined, washed with water and then with a saturated aqueous solution of sodium chloride, dried over magnesium sulfate and concentrated to dryness. 0.2 g of trans tert-butyl ester of (5-aminomethyl-adamantan-2-yl)-carbamic acid is obtained, and is used subsequently as it is.
M+H$^+$=281

1.5: Trans tert-butyl ester of [5-(methanesulfonylamino-methyl)adamantan-2-yl]-carbamic acid In a three-necked flask under nitrogen, 0.2 g of trans tert-butyl ester of (5-aminomethyl-adamantan-2-yl)-carbamic acid is dissolved in 7 ml of anhydrous dichloromethane. 0.12 ml of triethylamine is added and then the solution is cooled to 0° C. 0.06 ml of mesyl chloride is added dropwise. The mixture is stirred for 4 hours at room temperature and then hydrolyzed gently with ice. It is extracted with ethyl acetate until exhaustion of the aqueous phase. The organic phases are combined, washed with water and then with a saturated aqueous solution of sodium chloride, dried over magnesium sulfate and concentrated to dryness. The raw product obtained is chromatographed on silica gel, eluting with a gradient of methanol in dichloromethane in the range from 0 to 5%. 0.17 g of trans tert-butyl ester of [5-(methanesulfonylamino-methyl)adamantan-2-yl]-carbamic acid is obtained.
M+H$^+$=359

1.6: Trans N-(4-amino-adamantan-1-ylmethyl)-methanesulfonamide

In a three-necked flask under nitrogen, 0.16 g of trans tert-butyl ester of [5-(methanesulfonylamino-methyl)adamantan-2-yl]-carbamic acid is dissolved in 1 ml of anhydrous dichloromethane. 1.7 ml of 4N solution of hydrochloric acid in dioxane is added. The reaction mixture is stirred for 4 h at room temperature and then concentrated to dryness. 0.13 g of trans N-(4-amino-adamantan-1-ylmethyl)-methanesulfonamide is obtained, and is used subsequently as it is.

1.7: tert-Butyl ester of 4-(5-bromo-pyridin-2-yl)-3,4-dihydro-2H-quinoxaline-1-carboxylic acid 30 g of tert-butyl ester of 3,4-dihydro-2H-quinoxaline-1-carboxylic acid is put in 430 ml of N-methylpyrrolidinone at 0° C. under nitrogen. 30 g of potassium tert-butylate is added a little at a time, keeping the temperature below 10° C. It is stirred for 1.5 h at room temperature, then 850 ml of water and 800 ml of ethyl ether are added at 0° C. The aqueous phase is extracted with 800 ml of ethyl ether, then with 400 ml of ethyl ether. The organic phases are combined, then dried over magnesium sulfate and concentrated to dryness. 300 ml of pentane is added to the raw reaction product and the heterogeneous mixture obtained is sonicated with ultrasound for 5 min. The mixture is held at 5° C. for 48 h, then the solid is filtered, washed three times with pentane and then dried at 40° C. for 5 h. 35 g of tert-butyl ester of 4-(5-bromo-pyridin-2-yl)-3,4-dihydro-2H-quinoxaline-1-carboxylic acid is obtained.
M+H$^+$=392.0

1.8: tert-Butyl ester of 4-[5-(4-tert-butyl-piperazin-1-yl)pyridin-2-yl]-3,4-dihydro-2H-quinoxaline-1-carboxylic acid 28 g of tert-butyl ester of 4-(5-bromo-pyridin-2-yl)-3,4-dihydro-2H-quinoxaline-1-carboxylic and 9.7 g of 4-tert-butyl piperazine are put in 310 ml of toluene, then 2.5 g of tris(dibenzylideneacetone)dipalladium (0), 4.48 g of 2-dicyclohexylphosphino-2',6'-dimethoxybiphenyl and 9.17 g of sodium tert-butylate are added. The reaction mixture is heated at 110° C. for 16 h. Then ethyl acetate is added and the mixture is washed once with water and once with a saturated aqueous solution of sodium chloride. The organic phase is dried over magnesium sulfate and concentrated under reduced pressure. 41 g of tert-butyl ester of 4-[5-(4-tert-butyl-piperazin-1-yl)pyridin-2-yl]-3,4-dihydro-2H-quinoxaline-1-carboxylic acid is obtained, and is used without any other form of purification.
M+H$^+$=452.4

1.9: 1-[5-(4-tert-butyl-piperazin-1-yl)pyridin-2-yl]-1,2,3,4-tetrahydroquinoxaline 41 g of tert-butyl ester of 4-[5-(4-tert-butyl-piperazin-1-yl) pyridin-2-yl]-3,4-dihydro-2H-quinoxaline-1-carboxylic acid is put in a 1-liter three-necked flask under nitrogen atmosphere. 132 ml of dichloromethane is added, the reaction mixture is cooled on an ice bath and 257 ml of 4M solution of hydrochloric acid in dioxane is added dropwise. The temperature is allowed to return slowly to room temperature and then it is stirred for 2 h. The reaction mixture is diluted with dichloromethane, then it is cooled on an ice bath and saturated solution of NaHCO$_3$ is added to pH=8. It is left to settle and the aqueous phase is extracted with dichloromethane. The organic phases are washed with water, then the combined organic phases are dried over Na$_2$SO$_4$, filtered on a frit and concentrated. The raw product obtained is chromatographed on silica gel, eluting with a gradient in the range from 100% dichloromethane to a dichloromethane/ethyl acetate/methanol/concentrated aqueous ammonia mixture in the proportions 70/25/5/1 and then with a dichloromethane/methanol/concentrated aqueous ammonia mixture in the proportions 90/10/1. 0.3 g of 1-[5-(4-tert-butyl-piperazin-1-yl)pyridin-2-yl]-1,2,3,4-tetrahydroquinoxaline is obtained.

M+H$^+$=351.4

1.10 Trans [5-(Methanesulfonylamino-methyl)adamantan-2-yl]amide of 4-[5-(4-tert-butyl-piperazin-1-yl)pyridin-2-yl]-3,4-dihydro-2H-quinoxaline-1-carboxylic acid In a three-necked flask under nitrogen, 0.15 g of 1-[5-(4-tert-butyl-piperazin-1-yl)pyridin-2-yl]-1,2,3,4-tetrahydroquinoxaline is dissolved in 4 ml of anhydrous dichloromethane. 0.12 ml of triethylamine is added, then the solution is cooled to 0° C. 0.052 g of triphosgene is added twice. It is stirred for 3 h at room temperature, then 1.5 ml of dimethylformamide, 0.19 ml of N-ethyldiisopropylamine and 0.13 g of trans N-(4-amino-adamantan-1-ylmethyl)-methanesulfonamide are added. It is heated at 50° C. overnight. The reaction mixture is hydrolyzed with 50 ml of water and then it is extracted with ethyl acetate until exhaustion of the aqueous phase. The organic phases are combined, washed with water and then with a saturated aqueous solution of sodium chloride, dried over magnesium sulfate and concentrated to dryness. The raw product obtained is chromatographed on silica gel, eluting with a gradient in the range from 100% dichloromethane to a dichloromethane ethyl acetate methanol concentrated aqueous ammonia mixture in the proportions 70/25/5/1. 0.18 g of trans [5-(methanesulfonylamino-methyl)adamantan-2-yl]amide of 4-[5-(4-tert-butyl-piperazin-1-yl)pyridin-2-yl]-3,4-dihydro-2H-quinoxaline-1-carboxylic acid is obtained.

M+H$^+$=636

1.11: trans [5-(Methanesulfonylamino-methyl)adamantan-2-yl]amide hydrochloride of 4-[5-(4-tert-butyl-piperazin-1-yl)pyridin-2-yl]-3,4-dihydro-2H-quinoxaline-1-carboxylic acid In a three-necked flask under nitrogen, 0.18 g of trans (5-(methanesulfonylamino-methyl)adamantan-2-yl]amide of 4-[5-(4-tert-butyl-piperazin-1-yl)pyridin-2-yl]-3,4-dihydro-2H-quinoxaline-1-carboxylic acid is dissolved in 3 ml of dichloromethane. 1.4 ml of 0.2N solution of hydrochloric acid in diethyl ether is added at room temperature and it is stirred for 15 minutes. The reaction mixture is concentrated to dryness and then the residue is taken up in a minimum of ethyl acetate to obtain crystallization of the salt that formed. The precipitated solid is drained, washed with ethyl acetate and then dried under vacuum over phosphorus pentoxide. 0.183 g of trans [5-(methanesulfonylamino-methyl)adamantan-2-yl] amide hydrochloride of 4-[5-(4-tert-butyl-piperazin-1-yl)pyridin-2-yl]-3,4-dihydro-2H-quinoxaline-1-carboxylic acid is obtained.

MP=252° C., M+H$^+$=636.

1H NMR (400 MHz, DMSO-d6) δ ppm=10.28 (m, 1H), 8.09 (m, 1H), 7.48 (d, J=7.9 Hz, 2H), 7.18 (m, 2H), 6.94 (m, 2H), 6.85 (m, 1H), 6.06 (d, J=5.8 Hz, 1H), 4.01 to 3.34 (m, 8H), 3.19 (m, 4H), 2.87 (s, 3H), 2.63 (d, J=6 Hz, 2H), 2.09 to 1.69 (m, 5H), 1.67 to 1.27 (m, 17H)

Example 2

Trans (5-Carbamoylmethyl-adamantan-2-yl)amide of 4-[5-(4-cyclopropanesulfonyl-piperazin-1-yl)pyridin-2-yl]-3,4-dihydro-2H-quinoxaline-1-carboxylic acid (compound No. 3)

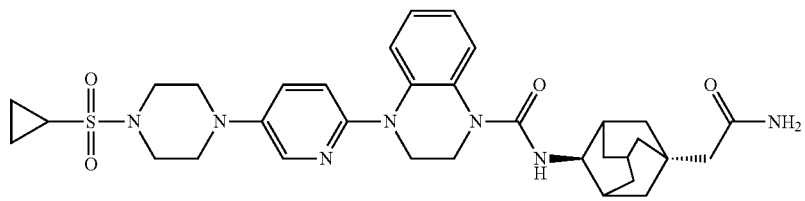 [SMILES: NC(=O)C[C@]12CC3CC(C1)[C@H](NC(=O)N1CCN(c4ccc(N5CCN(S(=O)(=O)C6CC6)CC5)cn4)c4ccccc41)C(C3)C2]

2.1: Trans 2-(4-Amino-adamantan-1-yl)acetamide

In a 25 ml flask, 0.318 g of trans tert-butyl of (5-cyanomethyl-adamantan-2-yl)-carbamic acid is put in 2 ml of 95% sulfuric acid. It is heated under reflux for 2 h. The solution is cooled to room temperature. 4 ml of ethanol is added and it is heated under reflux for 4 h. The reaction mixture is poured into water plus ice. The aqueous phase is evaporated and it is taken up in methanol mixed with dichloromethane and acetonitrile. It is filtered and the filtrate is partially evaporated again. It is filtered once more and the filtrate is evaporated to dryness, then taken up in methanol and dried over magnesium sulfate. 0.259 g of 85/15 mixture of trans 2-(4-amino-adamantan-1-yl) acetamide mixed with trans 2-(4-amino-adamantan-1-yl)acetic acid is obtained.

2.2: Trans (5-Carbamoylmethyl-adamantan-2-yl) amide of 4-[5-(4-cyclopropanesulfonyl-piperazin-1-yl)pyridin-2-yl]-3,4-dihydro-2H-quinoxaline-1-carboxylic acid In a 100 ml flask, 0.437 g of 1-[5-(4-cyclopropanesulfonyl-piperazin-1-yl)pyridin-2-yl]-1,2,3,4-tetrahydroquinoxaline (intermediate 7.5) is put in 18 ml of saturated solution of sodium hydrogen carbonate. 18 ml of dichloromethane is added. The solution is cooled in an ice bath. At +5° C., 0.86 ml of 20% phosgene solution in toluene is added. After 30 minutes, the reaction is complete. The reaction mixture is decanted. Dichloromethane is added to the aqueous phase and decanted again. The organic phases are then combined, dried over magnesium sulfate, filtered and evaporated to dryness. This raw reaction product is taken up in 10 ml of dimethylformamide. 0.95 ml of diisopropylethylamine is added. 0.259 g of 85/15 mixture of trans 2-(4-amino-adamantan-1-yl)acetamide mixed with trans 2-(4-amino-adamantan-1-yl)acetic acid is added. The solution is stirred at room temperature for two days. The reaction mixture is poured into water and extracted twice with ethyl acetate. The organic phase is washed twice with water, dried over magnesium sulfate, filtered and evaporated to dryness. The raw product obtained is chromatographed on silica gel, eluting with a gradient of methanol in dichloromethane varying from 1% to 10%. A product is obtained, which is then triturated in ethyl ether with a few drops of ethyl acetate. 0.269 g of trans (5-carbamoyl-methyl-adamantan-2-yl)amide of 4-[5-(4-cyclopropane-sulfonyl-piperazin-1-yl)pyridin-2-yl]-3,4-dihydro-2H-quinoxaline-1-carboxylic acid is obtained.

M+H$^+$=634, MP=120–135° C.

1H NMR (400 MHz, DMSO-d6) δ ppm=8.08 (m, 1H), 7.45 (m, 2H), 7.15 (m, 3H), 6.96 (m, 1H), 6.88 (m, 1H), 6.64 (s broad, 1H), 6.03 (d, J=6.5 Hz, 1H), 3.81 (m, 4H), 3.69 (m, 1H), 3.47 to 3.13 (m, 8H), 2.68 (m, 1H), 2.07 to 1.31 (m, 15H), 1.01 (m, 4H).

Example 3

Trans (5-Aminomethyl-adamantan-2-yl)amide of 4-[5-(4-cyclopropanesulfonyl-piperazin-1-yl)pyridin-2-yl]-3,4-dihydro-2H-quinoxaline-1-carboxylic acid (compound No. 4)

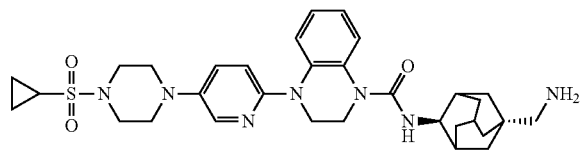 [SMILES: NC[C@]12CC3CC(C1)[C@H](NC(=O)N1CCN(c4ccc(N5CCN(S(=O)(=O)C6CC6)CC5)cn4)c4ccccc41)C(C3)C2]

3.1: tert-Butyl ester of {5-[(benzyl-phenylacetyl-amino)-methyl]adamantan-2-yl}-carbamic acid In a three-necked flask under nitrogen, 0.55 g of tert-butyl ester of [5-(benzylamino-methyl)adamantan-2-yl]-carbamic acid is dissolved in 1.75 ml of anhydrous dichloromethane. 0.25 ml of triethylamine is added and then 0.25 ml of benzyl chloroformate is added dropwise. The reaction mixture is stirred for 30 minutes at room temperature and then 0.12 ml of triethylamine and 0.12 ml of benzyl chloroformate are added. The reaction is continued for 30 minutes and then it is hydrolyzed gently with water. The reaction mixture is extracted with dichloromethane until exhaustion of the aqueous phase. The organic phases are combined, washed with a saturated aqueous solution of potassium hydrogen sulfate, with a saturated aqueous solution of sodium hydrogen carbonate, and with a saturated aqueous solution of sodium chloride, then dried over magnesium sulfate and concentrated to dryness. The raw product obtained is chromatographed on silica gel, eluting with a gradient of methanol in dichloromethane in the range from 0 to 2%. 0.32 g of tert-butyl ester of {5-[(benzyl-phenylacetyl-amino)-methyl]adamantan-2-yl}-carbamic acid is obtained.

M+H$^+$=505

3.2: N-(4-Amino-adamantan-1-ylmethyl)-N-benzyl-2-phenyl-acetamide

In a three-necked flask under nitrogen, 0.49 g of tert-butyl ester of {5-[(benzyl-phenylacetyl-amino)-methyl]adamantan-2-yl}-carbamic acid is dissolved in 1.7 ml of anhydrous dichloromethane. It is cooled to 0° C. and 3.64 ml of 4N solution of hydrochloric acid in dioxane is added. The reaction mixture is stirred for 1 h at room temperature and then concentrated to dryness. 20 ml of water is added, the reaction mixture is basified with potassium carbonate and it is extracted with dichloromethane until exhaustion of the aqueous phase. The organic phases are combined, washed with a saturated aqueous solution of sodium chloride, dried over magnesium sulfate and concentrated to dryness. 0.35 g of N-(4-amino-adamantan-1-ylmethyl)-N-benzyl-2-phenyl-acetamide is obtained, and is used subsequently as it is.

M+H$^+$=405

3.3: Trans {5-[(Benzyl-phenylacetyl-amino)-methyl]adamantan-2-yl}amide of 4-[5-(4-cyclopropane-sulfonyl-piperazin-1-yl)pyridin-2-yl]-3,4-dihydro-2H-quinoxaline-1-carboxylic acid In a three-necked flask under nitrogen, 0.36 g of 1-[5-(4-cyclopropanesulfonyl-piperazin-1-yl)pyridin-2-yl]-1,2,3,4-tetrahydroquinoxaline is dissolved in 8.5 ml of anhydrous dichloromethane. 0.25 ml of triethylamine is added and then the solution is cooled to 0° C. 0.106 g of triphosgene is added twice. It is stirred for 2 h 30 minutes at room temperature, then 8.5 ml of dimethylformamide, 0.39 ml of N-ethyldiisopropylamine and 0.35 g of trans N-(4-amino-adamantan-1-ylmethyl)-N-benzyl-2-phenyl-acetamide are added. It is heated at 60° C. overnight. The reaction mixture is hydrolyzed with 100 ml of water and then it is extracted with ethyl acetate until exhaustion of the aqueous phase. The organic phases are combined, washed with water and then with saturated aqueous solution of sodium chloride, dried over magnesium sulfate and concentrated to dryness. The raw product obtained is chromatographed on silica gel, eluting with a gradient of methanol in dichloromethane in the range from 0 to 5%. 0.42 g of trans {5-[(benzyl-phenylacetyl-amino)-methyl]adamantan-2-yl}amide of 4-[5-(4-cyclopropanesulfonyl-piperazin-1-yl)pyridin-2-yl]-3,4-dihydro-2H-quinoxaline-1-carboxylic acid is obtained.

M+H$^+$=831

3.4: (5-Aminomethyl-adamantan-2-yl)amide of 4-[5-(4-cyclopropanesulfonyl-piperazin-1-yl}pyridin-2-yl]-3,4-dihydro-2H-quinoxaline-1-carboxylic acid In a three-necked flask under nitrogen, 0.42 g of trans {5-[(benzyl-phenylacetyl-amino)-methyl]adamantan-2-yl}amide of 4-[5-(4-cyclopropanesulfonyl-piperazin-1-yl)pyridin-2-yl]-3,4-dihydro-2H-quinoxaline-1-carboxylic acid is dissolved in 5 ml of methanol. 0.076 g of 10% palladium on charcoal wetted to 50% with water is added, and then 0.48 g of ammonium formate. It is heated under reflux for 1 hour 30 minutes. The reaction mixture is filtered on a paper filter. The solution is concentrated to dryness. The residue is taken up in 50 ml of water, the reaction mixture is basified with potassium carbonate and it is extracted with dichloromethane until exhaustion of the aqueous phase. The organic phases are combined, washed with a saturated aqueous solution of sodium chloride, dried over magnesium sulfate and concentrated to dryness. The raw product obtained is chromatographed on silica gel, eluting with a gradient in the range from 100% dichloromethane to a dichloromethane/methanol/concentrated aqueous ammonia mixture in the proportions 95/5/0.5. 0.19 g of trans (5-aminomethyl-adamantan-2-yl)amide of 4-[5-(4-cyclopropanesulfonyl-piperazin-1-yl)pyridin-2-yl]-3,4-dihydro-2H-quinoxaline-1-carboxylic acid is obtained.

M+H$^+$=606

3.5: trans (5-Aminomethyl-adamantan-2-yl)amide hydrochloride of 4-[5-(4-cyclopropanesulfonyl-piperazin-1-yl)pyridin-2-yl]-3,4-dihydro-2H-quinoxaline-1-carboxylic acid In a three-necked flask under nitrogen, 0.18 g of trans {5-aminomethyl-adamantan-2-yl)amide of 4-[5-(4-cyclopropanesulfonyl-piperazin-1-yl)pyridin-2-yl]-3,4-dihydro-2H-quinoxaline-1-carboxylic acid is dissolved in 3 ml of dichloromethane. 1.54 ml of 0.2N solution of hydrochloric acid in diethyl ether is added at room temperature and it is stirred for 15 minutes. The reaction mixture is concentrated to dryness and then the residue is taken up in a minimum of ethyl acetate to obtain crystallization of the salt that formed. The precipitated solid is drained, washed with ethyl acetate and then dried under vacuum over phosphorus pentoxide. 0.188 g of trans (5-aminomethyl-adamantan-2-yl)amide hydrochloride of 4-[5-(4-cyclopropanesulfonyl-piperazin-1-yl)pyridin-2-yl]-3,4-dihydro-2H-quinoxaline-1-carboxylic acid is obtained.

M+H$^+$=606, MP=197° C.

1H NMR (400 MHz, DMSO-d6) δ ppm=8.04 (d, J=2.8 Hz, 1H), 7.88 (m, 3H), 7.49 (m, 2H), 7.17 (m, 2H), 6.94 (m, 2H), 6.14 (d, J=5.9 Hz, 1H), 4.07 to 3.66 (m, 6H), 3.37 (m, 4H), 3.25 (m, 4H), 2.68 (m, 1H), 2.01 (m, 2H), 1.92 (m, 1H), 1.81 (m, 2H), 1.69 to 1.49 (m, 6H), 1.42 (m, 2H), 1.08 to 0.93 (m, 4H)

Example 4

Trans 4-({4-[5-(4-Cyclopropanesulfonyl-piperazin-1-yl)pyridin-2-yl]-3,4-dihydro-2H-quinoxaline-1-carbonyl}amino)adamantan-1-yl ester of carbamic acid (compound No. 5)

4.1: Trans (5-Hydroxy-adamantan-2-yl)amide of 4-[5-(4-cyclopropanesulfonyl-piperazin-1-yl)pyridin-2-yl]-3,4-dihydro-2H-quinoxaline-1-carboxylic acid A solution under nitrogen of 40 ml of anhydrous dichloromethane containing 1.6 g of 1-[5-(4-cyclopropanesulfonyl-piperazin-1-yl)pyridin-2-yl]-1,2,3,4-tetrahydroquinoxaline is cooled to 0° C. 2.23 ml of triethylamine and 0.475 g of triphosgene are then added. After stirring at room temperature for 1.5 h, 0.816 g of trans 4-amino-adamantan-1-ol hydrochloride and 20 ml of anhydrous dimethylformamide are added. Stirring is maintained for 18 hours. The reaction mixture is heated at 35° C. for 4 hours. The solvents are evaporated under reduced pressure. The residue is taken up in water. The aqueous phase is extracted three times with dichloromethane. The organic phases are combined, washed three times with water, dried over sodium sulfate, filtered and concentrated to dryness. The residue obtained is purified by silica column chromatography, eluting with a mixture of dichloromethane/(dichloromethane/methanol 90/10) 90/10 to 20/80. 1.8 g of trans (5-hydroxy-adamantan-2-yl)amide of 4-[5-(4-cyclopropanesulfonyl-piperazin-1-yl)pyridin-2-yl]-3,4-dihydro-2H-quinoxaline-1-carboxylic acid is obtained.

(M+H$^+$)=593

4.2 Trans 4-({4-[5-(4-Cyclopropanesulfonyl-piperazin-1-yl)pyridin-2-yl]-3,4-dihydro-2H-quinoxaline-1-carbonyl}amino)adamantan-1-yl ester of carbamic acid A solution under nitrogen of 1.3 ml of anhydrous dichloromethane containing 0.15 g of trans (5-hydroxy-adamantan-2-yl)amide of 4-[5-(4-cyclopropanesulfonyl-piperazin-1-yl) pyridin-2-yl]-3,4-dihydro-2H-quinoxaline-1-carboxylic acid is cooled to 0° C. 0.04 ml (1.2 eq) of trichloro-acetyl isocyanate is added. After stirring for 18 hours at room temperature, the dichloromethane is evaporated. The residue is taken up in 1 ml of methanol and 1.5 ml of a saturated solution of potassium carbonate. After heating at 50° C. for 5 hours, the reaction mixture is cooled to room temperature and the solvents are evaporated. The residue is taken up in dichloromethane. The organic phase is washed with water, dried over sodium sulfate, filtered and concentrated to dryness in a rotary evaporator. The residue obtained is purified by silica column chromatography, eluting with a mixture of dichloromethane/(dichloromethane/methanol 90/10) 95/5 to 45/55. 0.07 g of trans 4-({4-(5-{4-cyclopropanesulfonyl-piperazin-1-yl)pyridin-2-yl]-3,4-dihydro-2H-quinoxaline-1-carbonyl}amino)adamantan-1-yl ester of carbamic acid is obtained.

M+H$^+$=636.

MP=decomposition starting from 106° C.

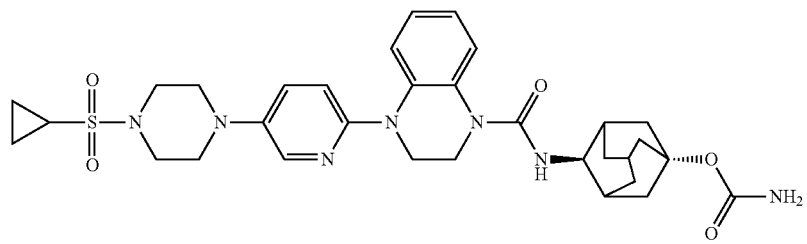 [SMILES: NC(=O)O[C@]12CC3CC(C1)[C@H](NC(=O)N1CCN(c4ccc(N5CCN(S(=O)(=O)C6CC6)CC5)cn4)c4ccccc41)C(C3)C2]

1H NMR (400 MHz, DMSO-d6) δ ppm=8.07 (d, J=2.9 Hz, 1H), 7.47 (dd, J=7.9 Hz and 1.5 Hz, 1H), 7.43 (dd, J=9 Hz and 3 Hz, 1H), 7.14 (m, 2H), 6.95 (m, 1H), 6.88 (m, 1H), 6.18 (m, 2H), 6.08 (d, J=6 Hz, 1H), 3.80 (m, 4H), 3.76 (m, 1H), 3.36 (m, 4H), 3.22 (m, 4H), 2.67 (m, 1H), 2.09 (m, 9H), 1.74 (m, 2H), 1.45 (m, 2H), 1.08 to 0.93 (m, 4H)

Example 5

Trans [5-(2,2,2-trifluoro-1-hydroxy-ethyl)adamantan-2-yl]amide of 4-[5-(4-tert-butyl-piperazin-1-yl)pyridin-2-yl]-3,4-dihydro-2H-quinoxaline-1-carboxylic acid (compound No. 6)

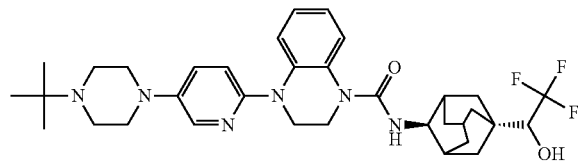 [SMILES: CC(C)(C)N1CCN(c2ccc(N3CCN(C(=O)N[C@H]4C5CC6CC4C[C@@](C(O)C(F)(F)F)(C6)C5)c4ccccc43)nc2)CC1]

5.1: Methyl ester of 4-({4-[5-(4-tert-butyl-piperazin-1-yl)pyridin-2-yl]-3,4-dihydro-2H-quinoxaline-1-carbonyl}amino)adamantane-1-carboxylic acid 1.16 g of 1-[5-(4-tert-butyl-piperazin-1-yl)pyridin-2-yl]-1,2,3,4-tetrahydroquinoxaline (intermediate 1.9), 33 ml of dichloromethane and 1.38 ml of triethylamine are put in a three-necked flask under nitrogen atmosphere. After cooling the mixture to −5° C. with an ice/acetone mixture, 0.524 g of triphosgene is added. The reaction mixture is stirred at room temperature for 3 h. The reaction mixture is concentrated under reduced pressure, then it is taken up in 23 ml of dimethylformamide and 1.38 ml of triethylamine. 0.811 g of methyl ester hydrochloride of trans 4-amino-adamantan-1-carboxylic acid is added. The reaction mixture is stirred at room temperature for 18 h. The mixture is diluted with 300 ml of saturated solution of sodium chloride and extracted 5 times with 50 ml of ethyl acetate. The ethyl acetate phases are combined and dried over sodium sulfate. After concentration, the raw reaction product is chromatographed on silica gel, eluting with a gradient of dichloromethane/methanol/ammonia solvents (100/0/0 to 90/10/1). 1.15 g of methyl ester of 4-({4-[5-(4-tert-butyl-piperazin-1-yl)pyridin-2-yl]-3,4-dihydro-2H-quinoxaline-1-carbonyl}amino)adamantane-1-carboxylic acid is obtained.

M+H+=587.2

5.2: Trans (5-hydroxymethyl-adamantan-2-yl)amide of 4-[5-(4-tert-butyl-piperazin-1-yl)pyridin-2-yl]-3,4-dihydro-2H-quinoxaline-1-carboxylic acid 1.14 g of methyl ester of 4-({4-[5-(4-tert-butyl-piperazin-1-yl)pyridin-2-yl]-3,4-dihydro-2H-quinoxaline-1-carbonyl}amino)adamantane-1-carboxylic acid and 19 ml of anhydrous tetrahydrofuran are put in a three-necked flask under nitrogen atmosphere. After cooling the mixture to −6° C. with an ice/acetone mixture, 2.33 ml of a 1M solution of LiAlH4 in tetrahydrofuran is added. The temperature of the reaction mixture is allowed to rise gradually to 20° C. After 3 h the reaction mixture is neutralized by adding a 10% solution of potassium hydrogen sulfate in water. The reaction mixture is then diluted with 150 ml of water, alkalized by adding sodium hydrogen carbonate and extracted with dichloromethane. The dichloromethane phase is dried over sodium sulfate and concentrated under reduced pressure. The raw product obtained is purified on silica gel, eluting with a gradient of dichloromethane/methanol/ammonia solvents (100/0/0 to 90/10/1). 0.8 g of trans (5-hydroxymethyl-adamantan-2-yl)amide of 4-[5-(4-tert-butyl-piperazin-1-yl)pyridin-2-yl]-3,4-dihydro-2H-quinoxaline-1-carboxylic acid is obtained.

M+H+=559.2

5.3: Trans (5-Formyl-adamantan-2-yl)amide of 4-[5-(4-tert-butyl-piperazin-1-yl)pyridin-2-yl]-3,4-dihydro-2H-quinoxaline-1-carboxylic acid 0.25 g of trans (5-hydroxymethyl-adamantan-2-yl)amide of 4-[5-(4-tert-butyl-piperazin-1-yl-pyridin-2-yl]-3,4-dihydro-2H-quinoxaline-1-carboxylic acid, 2.5 ml of 1-2 dichloroethane, 0.12 g of 4-angstrom molecular sieve and 0.078 g of N-methylmorpholine N-oxide are put in a three-necked flask under nitrogen atmosphere. The mixture is stirred for 10 min at room temperature and then 0.008 g of tetrapropylammonium perruthenate is added. The reaction mixture is stirred at room temperature for 4 h. After concentration the raw product is taken up in acetonitrile, and filtered on a silica pellet. 0.16 g of trans (5-formyl-adamantan-2-yl)amide of 4-[5-(4-tert-butyl-piperazin-1-yl)pyridin-2-yl]-3,4-dihydro-2H-quinoxaline-1-carboxylic acid is obtained.

M+H+=557.2

5.4: Trans [5-(2,2,2-trifluoro-1-hydroxy-ethyl)adamantan-2-yl]amide of 4-[5-(4-tert-butyl-piperazin-1-yl)pyridin-2-yl]-3,4-dihydro-2H-quinoxaline-1-carboxylic acid 0.16 g of trans (5-formyl-adamantan-2-yl)amide of 4-[5-(4-tert-butyl-piperazin-1-yl)pyridin-2-yl]-3,4-dihydro-2H-quinoxaline-1-carboxylic acid and 0.6 ml of anhydrous tetrahydrofuran are put in a three-necked flask under nitrogen atmosphere. The mixture is cooled in an ice bath and then 0.13 ml of trifluoromethyltrimethylsilane is added. After stirring for a few minutes, 0.14 ml of 1M solution of tetrabutylammonium fluoride in tetrahydrofuran is added. The reaction mixture is left, with stirring, until the next day.

Trifluoromethyltrimethylsilane and tetrabutylammonium are added regularly over a period of 48 h until there is no longer any reaction. At the end, the initial amounts of reagents had doubled. The reaction mixture is diluted with ethyl acetate and washed with water. The aqueous phases are combined and extracted with ethyl acetate. The organic phases are then washed with a saturated solution of sodium chloride and then dried over sodium sulfate. After concentration under reduced pressure, the raw product obtained is chromatographed on silica gel, eluting with a gradient of dichloromethane/methanol solvents (100/0 to 90/10). 0.015 g of trans [5-(2,2,2-trifluoro-1-hydroxy-ethyl)adamantan-2-yl]amide of 4-[5-(4-tert-butyl-piperazin-1-yl)pyridin-2-yl]-3,4-dihydro-2H-quinoxaline-1-carboxylic acid is obtained.

MP=192-196; M+H+=627.2,

1H NMR (400 MHz, DMSO-d6) δ ppm=8.03 (m, 1H), 7.44 (m, 1H), 7.37 (m, 1H), 7.11 (m, 2H), 6.94 (m, 1H), 6.86 (m, 1H), 6.11 (d, J=7.8 Hz, 1H), 6.06 (d, J=6 Hz, 1H), 3.79 (m, 4H), 3.71 (m, 1H), 3.47 (m, 1H), 3.11 (m, 4H), 2.66 (m, 4H), 1.99 (m, 2H), 1.89 (m, 1H), 1.83 to 1.63 (m, 8H), 1.44 (m, 2H), 1.06 (m, 9H)

Example 6

Trans [5-(2H-tetrazol-5-ylmethyl)adamantan-2-yl] amide of 4-[5-(4-tert-butyl-piperazin-1-yl)pyridin-2-yl]-3,4-dihydro-2H-quinoxaline-1-carboxylic acid (compound No. 7)

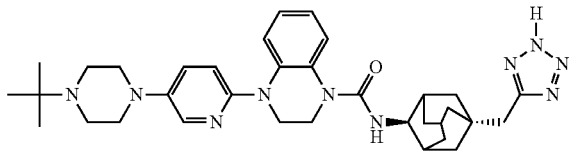 [SMILES: CC(C)(C)N1CCN(c2ccc(N3CCN(C(=O)N[C@H]4C5CC6CC4C[C@@](Cc4nn[nH]n4)(C6)C5)c4ccccc43)nc2)CC1]

6.1: Trans trifluoro-methanesulfonic acid 4-tert-butoxycarbonylamino-adamantan-1-yl methyl ester 4.86 g of trans tert-butyl ester of (5-hydroxymethyl-adamantan-2-yl)-carbamic acid is dissolved in 88 ml of dichloromethane. 2.8 ml of pyridine is added. The flask is immersed in an ice bath. At +4° C., 4.1 ml of trifluorosulfonic anhydride is added gently, using a syringe. It is stirred at room temperature for 3 h. The solution is poured into water, and extracted twice with dichloromethane. The organic phase is washed twice with a 1N solution of hydrochloric acid, once with water and once more with a saturated solution of sodium chloride. It is dried over sodium sulfate, filtered and evaporated to dryness. 6.29 g of trans trifluoro-methanesulfonic acid 4-tert-butoxycarbonylamino-adamantan-1-yl methyl ester mixed with 36% of starting product is obtained.
M−56+ACN+H$^+$=399

6.2: Trans tert-butyl ester of (5-cyanomethyl-adamantan-2-yl)-carbamic acid 6.29 g of trans trifluoro-methanesulfonic acid 4-tert-butoxycarbonylamino-adamantan-1-yl methyl ester is dissolved in 76 ml of dimethylformamide. 1 g of potassium cyanide is added at room temperature. The solution is stirred at room temperature for 2 days. The reaction mixture is poured into water and is extracted twice with ethyl acetate. The organic phase obtained is washed three times with water and once with a saturated solution of sodium chloride. It is dried over magnesium sulfate, filtered and evaporated to dryness. The raw product obtained is chromatographed on silica gel, eluting with a gradient of ethyl acetate in heptane varying from 0% to 50%. 1.56 g of trans tert-butyl ester of (5-cyanomethyl-adamantan-2-yl)-carbamic acid is obtained.
M−56+ACN+H$^+$=276

6.3: Trans tert-butyl ester of [5-(2H-tetrazol-5-ylmethyl)adamantan-2-yl]-carbamic acid 0.5 g of trans tert-butyl ester of (5-cyanomethyl-adamantan-2-yl)-carbamic acid is dissolved in 8 ml of toluene. 0.71 g of azidotrimethyltin is added. It is heated under reflux for 18 h. It is transferred to a sealed tube and is heated at 120° C. for 2 days. A further 0.35 g of azidotrimethyltin is added and it is heated at 130° C. for 4 h and then 18 h at 120° C. The solution is poured into water, and extracted three times with ethyl acetate. The organic phase is washed with water twice, dried over magnesium sulfate, filtered and evaporated to dryness. The raw product obtained is chromatographed on silica gel, eluting with a gradient of methanol in dichloromethane varying from 1% to 10%. 0.367 g of trans tert-butyl ester of [5-(2H-tetrazol-5-ylmethyl)adamantan-2-yl]-carbamic acid is obtained.
M−56+ACN+H$^+$=319

6.4: Trans tert-butyl ester of [5-(2-benzyl-2H-tetrazol-5-ylmethyl)-adamantan-2-yl]-carbamic acid and trans tert-butyl ester of [5-(1-benzyl-1H-tetrazol-5-ylmethyl)adamantan-2-yl]-carbamic acid 0.367 g of trans tert-butyl ester of [5-(2H-tetrazol-5-ylmethyl)adamantan-2-yl]-carbamic acid is put in 5.5 ml of acetone. 0.198 g of potassium carbonate and 0.16 ml of benzyl bromide are added in an ice bath. The solution is stirred at room temperature for 2 h. It is poured into water and extracted twice with ethyl acetate. The organic phase is washed twice with water, dried over magnesium sulfate, filtered and evaporated to dryness. The raw product obtained is chromatographed on silica gel, eluting with a gradient of ethyl acetate in heptane varying from 0% to 30% for 45 minutes then from 30% to 80% for 15 minutes. 0.489 g of a mixture of trans tert-butyl ester of [5-(2-benzyl-2H-tetrazol-5-ylmethyl)adamantan-2-yl]-carbamic acid and trans tert-butyl ester of [5-(1-benzyl-1H-tetrazol-5-ylmethyl)adamantan-2-yl]-carbamic acid is obtained.
M+H$^+$=424 and 424

6.5: Hydrochlorides of trans 5-(1-benzyl-1H-tetrazol-5-ylmethyl)adamantan-2-ylamine and of trans 5-(2-benzyl-2H-tetrazol-5-ylmethyl)adamantan-2-ylamine 0.466 g of a mixture of trans tert-butyl ester of [5-(2-benzyl-2H-tetrazol-5-ylmethyl)adamantan-2-yl]-carbamic acid and of trans tert-butyl ester of [5-(1-benzyl-1H-tetrazol-5-ylmethyl)adamantan-2-yl]-carbamic acid is put in 5.5 ml of dichloromethane. 5.5 ml of 4N hydrochloric acid in dioxane is added at room temperature. The solution is stirred for 18 h. It is evaporated to dryness. 0.312 g of a mixture of hydrochlorides of trans 5-(1-benzyl-1H-tetrazol-5-ylmethyl)adamantan-2-ylamine and of trans 5-(2-benzyl-2H-tetrazol-5-ylmethyl)adamantan-2-ylamine is obtained.
M+H$^+$=324 and 324

6.6: Trans [5-(2-benzyl-2H-tetrazol-5-ylmethyl)adamantan-2-yl]amide of 4-[5-(4-tert-butyl-piperazin-1-yl)pyridin-2-yl]-3,4-dihydro-2H-quinoxaline-1-carboxylic acid and trans [5-(1-benzyl-1H-tetrazol-5-ylmethyl)adamantan-2-yl]amide of 4-[5-(4-tert-butyl-piperazin-1-yl)pyridin-2-yl]-3,4-dihydro-2H-quinoxaline-1-carboxylic acid In a 50 ml three-necked flask, under inert atmosphere of nitrogen, 0.175 g of 1-[5-(4-tert-butyl-piperazin-1-yl)pyridin-2-yl]-1,2,3,4-tetrahydroquinoxaline (intermediate 1.9) is added to 5 ml of dichloromethane. 0.21 ml of triethylamine is added at 0° C. Then 0.059 g of triphosgene is added. The reaction mixture is stirred for 30 minutes at 0° C. and then at room temperature for 3 h. 0.24 ml of triethylamine is added again and 0.2 g of a mixture of hydrochlorides of trans 5-(1-benzyl-1H-tetrazol-5-ylmethyl)adamantan-2-ylamine and of trans 5-(2-benzyl-2H-tetrazol-5-ylmethyl)adamantan-2-ylamine is then added. For better solubility, 5 ml of dimethylformamide is added. The solution is stirred at room temperature for 3 h, then left to stand for two days. It is then poured into water and extracted twice with dichloromethane. The organic phase is washed three times with water, dried over magnesium sulfate, filtered and evaporated to dryness. The raw product obtained is chromatographed on silica gel, eluting with a gradient of methanol in dichloromethane varying from 1% to 10%. 0.259 g of a mixture of trans [5-(2-benzyl-2H-tetrazol-5-ylmethyl)adamantan-2-yl]amide of 4-[5-(4-tert-butyl-piperazin-1-yl)pyridin-2-yl]-3,4-dihydro-2H-quinoxaline-1-carboxylic acid and trans [5-(1-benzyl-1H-tetrazol-5-ylmethyl)adamantan-2-yl]amide of 4-[5-(4-tert-butyl-piperazin-1-yl)pyridin-2-yl]-3,4-dihydro-2H-quinoxaline-1-carboxylic acid is obtained.

M+H$^+$=701 and 701

6.7: Trans [5-(2H-tetrazol-5-ylmethyl)adamantan-2-yl]amide of 4-[5-(4-tert-butyl-piperazin-1-yl)pyridin-2-yl]-3,4-dihydro-2H-quinoxaline-1-carboxylic acid In a 250 ml Paar flask, 0.259 g of a mixture of trans [5-(2-benzyl-2H-tetrazol-5-ylmethyl)adamantan-2-yl]amide of 4-[5-(4-tert-butyl-piperazin-1-yl)pyridin-2-yl]-3,4-dihydro-2H-quinoxaline-1-carboxylic acid and of trans [5-(1-benzyl-1H-tetrazol-5-ylmethyl)adamantan-2-yl]amide of 4-[5-(4-tert-butyl-piperazin-1-yl)pyridin-2-yl]-3,4-dihydro-2H-quinoxaline-carboxylic acid is dissolved in 20 ml of methanol. Under inert atmosphere, 0.039 g of 10% palladium on charcoal is added. After 5 h under 45 psi of hydrogen at 35° C., then 1 h under 45 psi at 40° C., the reaction is stopped. The solution is filtered on a Whatman frit and evaporated to dryness. The raw product obtained is chromatographed on silica gel, eluting with a gradient of methanol in dichloromethane varying from 1% to 10% for 1 hour and from 10% to 20% for 30 minutes. The crystals are triturated in ethyl ether to which a few drops of ethyl acetate have been added. The precipitate is then drained and dried under vacuum at 40° C. 0.115 g of trans [5-(2H-tetrazol-5-ylmethyl)adamantan-2-yl]amide of 4-[5-(4-tert-butyl-piperazin-1-yl)pyridin-2-yl]-3,4-dihydro-2H-quinoxaline-1-carboxylic acid is obtained.

M+H$^+$=611, MP=160-170° C.

1H NMR (400 MHz, DMSO-d6) δ ppm=8.02 (d, J=3 Hz, 1H), 7.43 (dd, J=8 Hz and 1.5 Hz, 1H); 7.36 (dd, J=9 Hz and 3 Hz, 1H); 7.10 (m, 2H), 6.93 (m, 1H), 6.85 (m, 1H), 6.03 (d, J=5.9 Hz, 1H), 3.78 (m, 4H), 3.66 (m, 1H), 3.12 (m, 4H), 2.69 (m, 4H), 2.66 (s, 2H), 1.96 (m, 2H), 1.86 (m, 1H), 1.73 (m, 2H), 1.62 to 1.31 (m, 9H), 1.08 (s, 9H)

Example 7

Trans (5-methoxycarbamoyl-adamantan-2-yl)amide of 4-[5-(4-cyclopropanesulfonyl-piperazin-1-yl)pyridin-2-yl]-3,4-dihydro-2H-quinoxaline-1-carboxylic acid (compound No. 8)

7.1: tert-Butyl ester of 4-(5-bromo-pyridin-2-yl)-3,4-dihydro-2H-quinoxaline-1-carboxylic acid 16 g of tert-butyl ester of 3,4-dihydro-2H-quinoxaline-1-carboxylic acid is put in a 1-liter three-necked flask, under nitrogen atmosphere. 325 ml of pyrrolidinone and 14.70 ml of 5-bromo-2-fluoropyridine are added. It is cooled in an ice bath. 15.93 g of potassium tert-butylate is added a little at a time. The reaction mixture is stirred cold for 1 h, then the reaction mixture is allows to return to room temperature. It is stirred for 1 h. It is cooled in an ice bath and is hydrolyzed slowly. The organic phase is extracted with ethyl ether. The combined organic phases are washed with water, then with saturated NaCl solution. The reaction mixture is dried, with stirring, over Na$_2$SO$_4$, then filtered on a frit and concentrated under reduced pressure. 10.1 g of tert-butyl ester of 4-(5-bromo-pyridin-2-yl)-3,4-dihydro-2H-quinoxaline-1-carboxylic acid is obtained in the form of a white solid, after purification on a silica column (heptane/EtOAc gradient: 5 to 20% of EtOAc).

M+H$^+$=392

7.2: tert-Butyl ester of 4-cyclopropanesulfonyl-piperazin-1-carboxylic acid 8 g of tert-butyl ester of piperazine-1-carboxylic acid is put in a 1-liter three-necked flask, under nitrogen atmosphere. 330 ml of dichloromethane is added, then 8.9 ml of triethylamine. The reaction mixture is cooled in an ice bath. 5.25 ml of cyclopropanesulfonyl chloride is added dropwise. The temperature is allowed to return slowly to room temperature and then the reaction mixture is stirred for 4.5 h. The reaction mixture is diluted with dichloromethane. The combined organic phases are washed with water, then with saturated NaCl solution, and then dried over Na$_2$SO$_4$, filtered on a frit and concentrated under reduced pressure. 13.94 g of tert-butyl ester of 4-cyclopropanesulfonyl-piperazine-1-carboxylic acid is obtained in the form of a white powder.

M+H (−Boc)=191

7.3: 1-Cyclopropanesulfonyl-piperazine hydrochloride 14.37 g of tert-butyl ester of 4-cyclopropanesulfonyl-piperazine-1-carboxylic acid is put in a 2-liter three-necked flask, under nitrogen atmosphere. 412 ml of dichloromethane is added. The reaction mixture is cooled in an ice bath and 4M hydrochloric acid in solution in dioxane is added dropwise. The reaction mixture is allowed to return gradually to room temperature. The reaction mixture is stirred for 2.5 h, then evaporated and concentrated. The residue is taken up in a small amount of ethyl ether, triturated and then filtered and dried. 10.25 g of 1-cyclopropanesulfonyl-piperazine hydrochloride is obtained in the form of a white powder.

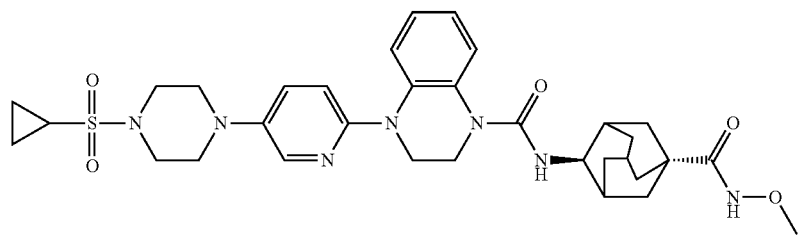 [SMILES: CONC(=O)[C@]12CC3CC(C1)[C@H](NC(=O)N1CCN(c4ccc(N5CCN(S(=O)(=O)C6CC6)CC5)cn4)c4ccccc41)C(C3)C2]

7.4: tert-Butyl ester of 4-[5-(4-cyclopropanesulfonyl-piperazin-1-yl)pyridin-2-yl]-3,4-dihydro-2H-quinoxaline-1-carboxylic acid 11.42 g (29.26 mmol, 1 eq) of tert-butyl ester of 4-(5-bromo-pyridin-2-yl)-3,4-dihydro-2H-quinoxaline-1-carboxylic acid is put in a 1-liter three-necked flask, under nitrogen atmosphere. 146 ml of anhydrous toluene is added. 7.63 g (33.65 mmol, 1.15 eq) of 1-cyclopropanesulfonyl-piperazine hydrochloride is added, and then 8.43 g (87.78 mmol, 3 eq) of NaOtBu, 1.92 g (4.68 mmol, 0.16 eq) of S-Phos then 1.07 g (1.17 mmol, 0.04 eq) of Pd$_2$(dba)$_3$. The reaction mixture is heated at 115° C. for 1 h40. The temperature of the reaction mixture is allowed to return slowly to room temperature. It is filtered on Celite, concentrated, and then the filtrate is washed with water and then with saturated NaCl solution. It is dried over Na$_2$SO$_4$, filtered on a frit and concentrated. The desired product is obtained in the form of white powder, after purification on a silica column (cyclohexane/EtOAc gradient: 30 to 75% of EtOAc) at a yield of 70% (m=10.27 g).
M+H$^+$=501

7.5: 1-[5-(4-cyclopropanesulfonyl-piperazin-1-yl)pyridin-2-yl]-1,2,3,4-tetrahydroquinoxaline 6.14 g of tert-butyl ester of 4-[5-(4-cyclopropanesulfonyl-piperazin-1-yl)pyridin-2-yl]-3,4-dihydro-2H-quinoxaline-1-carboxylic acid is put in a 1-liter three-necked flask under nitrogen atmosphere. 102 ml of dichloromethane is added, it is cooled in an ice bath and 92 ml of a 4M solution of hydrochloric acid in dioxane is added dropwise. The temperature of the reaction mixture is allowed to return slowly to room temperature and then it is stirred for 5 h. The reaction mixture is diluted with dichloromethane, then cooled in an ice bath. Then a saturated solution of NaHCO$_3$ is added to pH=8. It is decanted and the aqueous phase is extracted with dichloromethane. The water-based organic phases are washed, dried over Na$_2$SO$_4$, filtered on a frit and concentrated. 4.92 g of 1-[5-(4-cyclopropanesulfonyl-piperazin-1-yl)pyridin-2-yl]-1,2,3,4-tetrahydroquinoxaline is obtained in the form of a white solid.
M+H$^+$=400

7.6: trans Methyl ester hydrochloride of 4-amino-adamantan-1-carboxylic acid 2.65 g of trans 4-amino-adamantan-1-carboxylic acid is put in a 1-liter three-necked flask, under nitrogen atmosphere. 425 ml of methanol is added, then it is cooled on an ice bath. 1.10 ml of thionyl chloride is added dropwise. When the reaction mixture is clear, the ice bath is withdrawn and the reaction mixture is heated under reflux for 3.5 h. The temperature of the reaction mixture is allowed to return slowly to room temperature. It is concentrated and then triturated in ethyl ether and a few ml of ethanol, it is filtered on a frit, concentrated and then the product obtained is dried. 1.6 g of trans methyl ester hydrochloride of 4-amino-adamantan-1-carboxylic acid is obtained in the form of a white solid.
M+H$^+$=246

7.7: Trans methyl ester of 4-({4-[5-(4-cyclopropane-sulfonyl-piperazin-1-yl)pyridin-2-yl]-3,4-dihydro-2H-quinoxaline-carboxyl}amino)adamantan-1-carboxylic acid 2 g of 1-[5-(4-cyclopropanesulfonyl-piperazin-1-yl)pyridin-2-yl]-1,2,3,4-tetrahydroquinoxaline is put in a 500 ml three-necked flask, under nitrogen atmosphere. 50 ml of dichloromethane and 2.09 ml of triethylamine are added. The reaction mixture is cooled in an ice bath, then 0.74 g of triphosgene is added. The temperature of the reaction mixture is allowed to return slowly to room temperature. It is stirred for 1.5 h. Then 1.59 g of trans N-4-methyl-amino-adamantane-1-carboxylate is added in the form of hydrochloride dissolved hot in 50 ml of DMF in the presence of 2.09 ml of triethylamine. The reaction mixture is stirred at room temperature for 1 h and 20 min. The reaction mixture is concentrated and then taken up in EtOAc. The organic phase is washed with water, then dried over Na$_2$SO$_4$, filtered on a frit and concentrated. 2.74 g of trans methyl ester of 4-({4-[5-(4-cyclopropanesulfonyl-piperazin-1-yl)pyridin-2-yl]-3,4-dihydro-2H-quinoxaline-carboxyl}amino)adamantan-1-carboxylic acid is obtained in the form of a white powder, after purification on a silica column (gradient of dichloromethane/CH$_2$Cl$_2$/EtOAc/MeOH 75/25/5: 5 to 80% of CH$_2$Cl$_2$/EtOAc/MeOH 75/25/5).
M+H$^+$=635

7.8: trans 4-({4-(5-{4-Cyclopropanesulfonyl-piperazin-1-yl)pyridin-2-yl)-3,4-dihydro-2H-quinoxaline-1-carbonyl}amino)adamantan-1-carboxylic acid 2.92 g of trans methyl ester of 4-({4-[5-(4-cyclopropanesulfonyl-piperazin-1-yl)pyridin-2-yl]-3,4-dihydro-2H-quinoxaline-carboxyl}amino)adamantan-1-carboxylic acid is put in a 500 ml three-necked flask, under nitrogen atmosphere. 23 ml of THF and 11.5 ml of methanol are added. It is cooled in an ice bath. 335 mg of lithium hydroxide in solution in 11.5 ml of water is added. The reaction mixture is allowed to return slowly to room temperature. The reaction mixture is then stirred for 23 h and then concentrated. Then water is added and then SO$_2$ to pH=4-5. The precipitate obtained is triturated with a small amount of water, filtered and dried. 2.71 g of trans 4-({4-(5-(4-cyclopropanesulfonyl-piperazin-1-yl)pyridin-2-yl)-3,4-dihydro-2H-quinoxaline-1-carbonyl}amino)adamantan-1-carboxylic acid is obtained in the form of a white solid.
M+H$^+$=621

7.9: trans (5-Methoxycarbamoyl-adamantan-2-yl)amide of 4-[5-(4-cyclopropanesulfonyl-piperazin-1-yl)pyridin-2-yl]-3,4-dihydro-2H-quinoxaline-1-carboxylic acid 0.40 g of trans 4-({4-(5-(4-cyclopropanesulfonyl-piperazin-1-yl)-pyridin-2-yl)-3,4-dihydro-2H-quinoxaline-1-carbonyl}amino)adamantan-1-carboxylic acid is put in a 50 ml flask, under nitrogen atmosphere. 4 ml of dichloromethane and 3 ml of acetonitrile are added. 0.10 g of methoxyamine hydrochloride, 0.24 g of EDC, 0.19 g of HOBt and 0.72 ml of triethylamine are added. The reaction mixture is stirred at room temperature for 2 days. The reaction mixture is concentrated, and is then taken up in dichloromethane; the organic phase is washed with water, dried over Na$_2$SO$_4$, filtered on a frit and concentrated. After purification on silica column (gradient: dichloromethane/CH$_2$Cl$_2$/MeOH/NH$_4$OH 80/20/2: 5 to 45% of CH$_2$Cl$_2$/MeOH/NH$_4$OH 80/20/2), then trituration in ethyl ether, filtration and drying, 0.22 g of trans (5-methoxy[carbamoyl-adamantan-2-yl)amide of 4-[5-(4-cyclopropane-sulfonyl-piperazin-1-yl)pyridin-2-yl]-3,4-dihydro-2H-quinoxaline-1-carboxylic acid is obtained in the form of a white powder.
M+H$^+$=650, MP: 125-163° C.

1H NMR (400 MHz, DMSO-d6) δ ppm=10.78 (s, 1H), 8.08 (d, J=3 Hz, 1H), 7.47 (dd, J=8 Hz and 1.5 Hz, 1H), 7.43 (dd, J=9 Hz and 3 Hz, 1H), 7.14 (m, 2H), 6.95 (m, 1H), δ 6.88 (m, 1H), 6.09 (d, J=6 Hz, 1H), 3.81 (m, 4H), 3.73 (m, 1H), 3.56 (s, 3H), 3.36 (m, 4H), 3.22 (m, 4H), 2.67 (m, 1H), 2.00 (m, 2H), 1.93 to 1.70 (m, 9H), 1.45 (m, 2H), 1.08 to 0.93 (m, 4H)

Example 8

Trans (5-methanesulfonylamino-adamantan-2-yl) amide of 4-[5-(4-tert-butyl-piperazin-1-yl)pyridin-2-yl]-3,4-dihydro-2H-quinoxaline-1-carboxylic acid (compound No. 9)

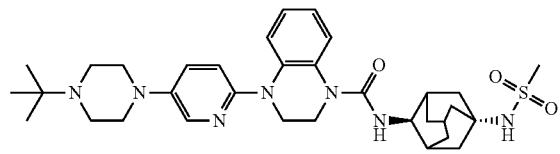 [SMILES: CC(C)(C)N1CCN(c2ccc(N3CCN(C(=O)N[C@H]4C5CC6CC4C[C@@](NS(C)(=O)=O)(C6)C5)c4ccccc43)nc2)CC1]

8.1: Trans tert-butyl ester of (5-amino-adamantan-2-yl)-carbamic acid 0.7 g of trans benzyl ester of (4-tert-butoxycarbonylamino-adamantan-1-yl)-carbamic acid is put in 18 ml of methanol and then 0.44 g of ammonium formate and 0.372 g of 10% palladium on charcoal (50% wet) are added. The reaction mixture is refluxed for two hours. The palladium is then filtered and is rinsed three times with methanol and the mixture is concentrated. 0.473 g of trans tert-butyl ester of (5-amino-adamantan-2-yl)-carbamic acid is obtained, which is used without any other form of purification.

M+H$^+$=267

8.2: trans tert-butyl ester of (5-methanesulfonylamino-adamantan-2-yl)-carbamic acid 0.45 g of trans tert-butyl ester of (5-amino-adamantan-2-yl)-carbamic acid is put in 8.45 ml of dichloromethane, then 0.28 ml of triethylamine and 0.14 ml of methane sulfonyl chloride are added. The reaction mixture is then stirred at room temperature for 18 hours, then water, dichloromethane and a saturated solution of sodium chloride are added to the mixture; the aqueous phase is extracted three times with dichloromethane. The organic phases are combined, then dried over magnesium sulfate and concentrated under vacuum. The raw product obtained is chromatographed on silica gel, eluting with a gradient of a heptane/ethyl acetate mixture (0 to 50/50). 0.5 g of trans tert-butyl ester of (5-methanesulfonylamino-adamantan-2-yl)-carbamic acid is obtained.

M+H$^+$=289

8.3: Trans N-(4-Amino-adamantan-1-yl)-methanesulfonamide 0.495 g of trans tert-butyl ester of (5-methanesulfonylamino-adamantan-2-yl)-carbamic acid is stirred with 5.39 ml of 4N hydrochloric acid in dioxane for twenty minutes. It is concentrated under reduced pressure, obtaining 0.395 g of raw trans N-(4-amino-adamantan-1-yl)-methanesulfonamide, which is used without any other form of purification.

8.4: Trans (5-methanesulfonylamino-adamantan-2-yl)amide of 4-[5-(4-tert-butyl-piperazin-1-yl)pyridin-2-yl]-3,4-dihydro-2H-quinoxaline-1-carboxylic acid 0.430 g of 1-[5-(4-tert-butyl-piperazin-1-yl)pyridin-2-yl]-1,2,3,4-tetrahydroquinoxaline is put in 12.23 ml of dichloromethane and 0.51 ml of triethylamine, then 0.181 g of triphosgene is added at 0° C. The reaction mixture is stirred at room temperature under nitrogen atmosphere for 15 minutes to form 4-[5-(4-tert-butyl-piperazin-1-yl)pyridin-2-yl]-3,4-dihydro-2H-quinoxaline-1-carbonyl chloride. 0.378 g of trans N-(4-amino-adamantan-1-yl)-methanesulfonamide is prepared in 10 ml of dimethyl formamide and 0.51 ml of triethylamine under nitrogen atmosphere which is heated to dissolve it. The hot mixture is added to the reaction mixture containing 4-[5-(4-tert-butyl-piperazin-1-yl)pyridin-2-yl]-3,4-dihydro-2H-quinoxaline-1-carbonyl chloride and it is stirred for two hours. Water and sodium chloride are added, and it is extracted three times with dichloromethane; the organic phases are combined and then dried over magnesium sulfate, then concentrated under reduced pressure. The 0.829 g of raw product is chromatographed on silica gel, eluting with a gradient of a dichloromethane/(dichloromethane-methanol 90:10) mixture from 0 to 100%. 0.4184 g of trans (5-methanesulfonylamino-adamantan-2-yl)amide of 4-[5-(4-tert-butyl-piperazin-1-yl)pyridin-2-yl]-3,4-dihydro-2H-quinoxaline-1-carboxylic acid is obtained.

MP=165° C.

M+H$^+$=622-623.

1H NMR (400 MHz, DMSO-d6) δ ppm=8.02 (d, J=3 Hz, 1H), 7.44 (dd, J=7.9 Hz and 1.5 Hz, 1H), 7.36 (dd, J=9 Hz and 3 Hz, 1H), 7.10 (m, 2H), 6.93 (m, 1H), 6.86 (m, 2H), 6.06 (d, J=5.6 Hz, 1H), 3.79 (m, 4H), 3.72 (m, 1H), 3.11 (m, 4H), 2.95 (s, 3H), 2.66 (m, 4H), 2.09 to 1.85 (m, 9H), 1.73 (m, 2H), 1.42 (m, 2H), 1.06 (m, 9H)

Example 9

Trans [5-(3-methyl-[1,2,4]oxadiazol-5-yl)adamantan-2-yl]amide of 4-[5-(4-cyclopropanesulfonyl-piperazin-1-yl)pyridin-2-yl]-3,4-dihydro-2H-quinoxaline-1-carboxylic acid (compound No. 10)

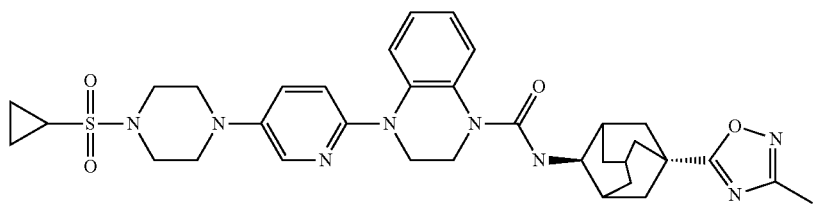 [SMILES: Cc1noc([C@]23CC4CC(C2)[C@H](NC(=O)N2CCN(c5ccc(N6CCN(S(=O)(=O)C7CC7)CC6)cn5)c5ccccc52)C(C4)C3)n1]

0.149 g of trans 4-({4-[5-(4-cyclopropanesulfonyl-piperazin-1-yl)pyridin-2-yl]-3,4-dihydro-2H-quinoxaline-1-carbonyl)amino)adamantane-1-carboxylic acid (intermediate 7.8) is put in 2.4 ml of toluene, then 0.021 g of N-hydroxy-acetamidine, 0.044 g of benzotriazol-1-ol alcohol hydrate, 0.036 g of diisopropyl-carbodiimide and 2.4 ml of dichloromethane are added, then the reaction mixture is stirred for 3.5 h at room temperature, then it is heated at 50° C. for 18 h. 0.042 g of N-hydroxy-acetamidine is added and it is heated at 50° C. for 18 h. The reaction mixture is concentrated under reduced pressure, and dichloromethane and water are added. The aqueous phase is extracted three times with dichloromethane, the organic phase is washed with water and saturated aqueous solution of sodium chloride. The organic phase is dried over magnesium sulfate and is concentrated under vacuum. 0.224 g of trans (5-{1-[hydroxyimino]-ethylcarbamoyl}adamantan-2-yl)amide of 4-[5-(4-cyclopropanesulfonyl-piperazin-1-yl)pyridin-2-yl]-3,4-dihydro-2H-quinoxaline-1-carboxylic acid is obtained (M+H$^+$=677), which is put in 4.73 ml of an ethanol-water mixture (4:1) with 0.0271 g of sodium acetate. The reaction mixture is heated under reflux for 18 h. The mixture is concentrated under reduced pressure, water is added and it is extracted three times with ethyl acetate. The organic phase is dried over magnesium sulfate and is concentrated under vacuum. The raw product obtained is chromatographed on silica gel, eluting with a mixture of solvents heptane/heptane-ethyl acetate-methanol (4/5/1). 0.111 g of trans [5-(3-methyl-[1,2,4]oxadiazol-5-yl)adamantan-2-yl]amide of 4-[5-(4-cyclopropanesulfonyl-piperazin-1-yl)pyridin-2-yl]-3,4-dihydro-2H-quinoxaline-1-carboxylic acid is obtained.

MP=135° C.; M+H$^+$=659.

1H NMR (400 MHz, DMSO-d6) δ ppm=8.08 (d, J=3 Hz, 1H), 7.49 (dd, J=8 Hz and 1.5 Hz, 1H), 7.43 (dd, J=9 Hz and 3 Hz, 1H), 7.15 (m, 2H), 6.95 (m, 1H), 6.89 (m, 1H), 6.19 (d, J=5.7 Hz, 1H), 3.82 (m, 5H), 3.36 (m, 4M), 3.23 (m, 4H), 2.67 (m, 1H), 2.32 (s, 3H), 2.17 to 1.94 (m, 9H), 1.88 (m, 2H), 1.56 (m, 2H), 1.08 to 0.83 (m, 4H)

The table given below illustrates the chemical structures and the physical properties of some compounds according to the invention, corresponding to formula (I), in which $R_{2b}$ represents a hydrogen atom, and being in the form of free bases or of salified compound:

in column "A", "—" represents a single bond;
base corresponds to the nonsalified molecule;
dec. corresponds to a decomposition temperature;
HCl represents a hydrochloride;
Me represents a methyl group;
MP denotes the melting point of the compound, expressed in degrees Celsius;
Salt corresponds to the form of the compound that can be in the form of the base or in salified form, for example a hydrochloride;
M+H$^+$ represents the mass of the compound, obtained by LC-MS (Liquid Chromatography-Mass Spectroscopy).

| N° | A | $R_{1a}$ | $R_{2a}$ | $R_{1b}$ | $R_{1c}$ | $R_{2c}$ | $R_3$ | $R_4$ | $R_8$ | $Ar_1$ |
|---|---|---|---|---|---|---|---|---|---|---|
| 6 | — | H | H | H | H | tert-butyl | H | —C(OH)(CF$_3$) (trans) | H | pyridine (N-A) |
| 7 | — | H | H | H | H | tert-butyl | H | —CH$_2$-tetrazole-NH (trans) | H | pyridine (N-A) |
| 8 | — | H | H | H | H | cyclopropylsulfonyl | H | —CONHOMe (trans) | H | pyridine (N-A) |
| 9 | — | H | H | H | H | tert-butyl | H | —NHSO$_2$Me (trans) | H | pyridine (N-A) |
| 10 | — | H | H | H | H | cyclopropylsulfonyl | H | 3-methyl-[1,2,4]oxadiazol-5-yl (trans) | H | pyridine (N-A) |

| N° | $Ar_2$ | Salt | MP (° C.) | M + H$^+$ | Synthesis |
|---|---|---|---|---|---|
| 6 | piperazine (A-N, N—$R_{1c}$) | Base | 192-196 | 627 | Method 3 |

| 7 |  | Base | 160-170 | 611 | Method 1 |
| 8 | 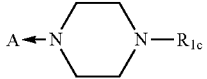 | Base | 125-163 | 650 | Method 5 |
| 9 | 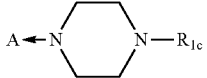 | Base | 165 | 62 | Method 1 |
| 10 | 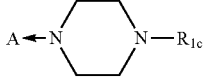 | Base | 135 | 659 | Method 6 |

The compounds according to the invention have undergone pharmacological tests for determining their inhibitory effect on the enzyme 11βHSD1, which is involved in lipid metabolism and in glucose metabolism.

These tests consisted of measuring the inhibitory activity in vitro of compounds of the invention on the enzyme 11βHSD1 using a Scintillation Proximity Assay (SPA) in 384-well format. The recombinant 11βHSD1 protein was produced in S. Cerevisiae yeast. The reaction was carried out by incubating the enzyme in the presence of $^3$H-cortisone and NADPH, in the absence or in the presence of increasing concentration of inhibitor. SPA beads coupled to an antimouse antibody, pre-incubated with an anticortisol antibody, made it possible to measure the amount of cortisol formed during the reaction.

The inhibitory activity with respect to the enzyme 11βHSD1 is given by the concentration that inhibits 50% of the activity of 11βHSD1 ($IC_{50}$).

The $IC_{50}$ values of the compounds of the invention are presented in the following table:

| Compound No. | 11βHSD1-HR $IC_{50}$ nM |
|---|---|
| 1 | 68 |
| 2 | 32 |
| 3 | 21 |
| 4 | 23 |
| 5 | 11 |
| 6 | 57 |
| 7 | 45 |
| 8 | 204 |
| 9 | 31 |
| 10 | 720 |

It therefore appears that the compounds according to the invention have an inhibitory activity on the enzyme 11βHSD1. The compounds according to the invention can therefore be used for preparing medicinal products, in particular medicinal products that are inhibitors of the enzyme 11βHSD1.

Thus, according to another of its aspects, the invention relates to medicinal products that comprise a compound of formula (I), or a salt of addition of the latter with a pharmaceutically acceptable acid or base, or a hydrate or a solvate of the compound of formula (I).

These medicinal products find application in therapeutics, notably in the treatment and prevention of obesity, diabetes, microcirculatory disorders, insulin resistance, metabolic syndrome, Cushing syndrome, hypertension, atherosclerosis, cognition and dementia, glaucomas, osteoporosis, lipodystrophy, cardiac hypertrophy, heart failure, liver diseases, and certain infectious diseases by increasing the effectiveness of the immune system or for promoting wound healing.

According to another of its aspects, the present invention relates to pharmaceutical compositions comprising, as active principle, a compound according to the invention. These pharmaceutical compositions contain an effective dose of at least one compound according to the invention or a pharmaceutically acceptable salt, a hydrate or solvate of said compound, as well as at least one pharmaceutically acceptable excipient. Said excipients are selected, depending on the pharmaceutical form and the desired method of administration, from the usual excipients that are known by a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or optionally a salt, solvate or hydrate thereof, can be administered as a unit dosage form, mixed with conventional pharmaceutical excipients, to animals and to human beings for preventing or treating the aforementioned disorders or diseases.

The appropriate unit dosage forms comprise forms for administration by the oral route, such as tablets, soft or hard capsules, powders, granules and oral solutions or suspensions, forms for sublingual, buccal, intratracheal, intraocular, intranasal administration, administration by inhalation, forms for topical, transdermal, subcutaneous, intramuscular or intravenous administration, forms for rectal administration and implants. For topical application, the compounds according to the invention can be used in creams, gels, ointments or lotions.

As an example, a unit dosage form of a compound according to the invention in tablet form can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The invention claimed is:
1. A compound corresponding to formula (I):

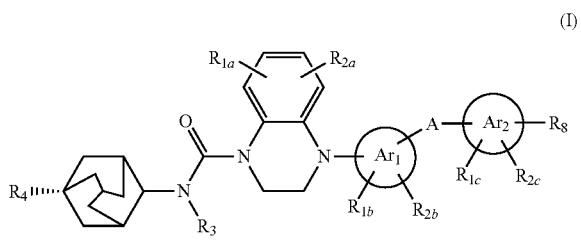

in which:
A represents a bond, an oxygen atom or an —O—CH$_2$— group,
Ar$_1$ represents a phenyl or heteroaryl group,
Ar$_2$ represents a phenyl group, a heteroaryl group or a heterocycloalkyl group,
R$_{1a,1b,1c}$ and R$_{2a,2b,2c}$, which may be identical or different, each represent a hydrogen or halogen atom or an alkyl group, cycloalkyl, -alkyl-cycloalkyl optionally substituted with one or more halogen atoms; —OR$_5$; hydroxy-alkyl; alkoxy-alkyl; alkoxy-alkoxy; haloalkyl; —O-haloalkyl; oxo; —CO-alkyl; —CO-alkyl-NR$_6$R$_7$; —CO-haloalkyl; —COOR$_5$; alkyl-COOR$_5$; —O-alkyl-COOR$_5$; —SO$_2$-alkyl; —SO$_2$-cycloalkyl; —SO$_2$-alkyl-cycloalkyl; —SO$_2$-alkyl-OR$_5$; —SO$_2$-alkyl-COOR$_5$; —SO$_2$-alkyl-NR$_6$R$_7$; —SO$_2$-haloalkyl; alkyl-SO$_2$-alkyl; —SO$_2$—NR$_6$R$_7$; —SO$_2$-alkyl-alkoxy-alkoxy; —CONR$_6$R$_7$; -alkyl-CONR$_6$R$_7$ or —O-alkyl-NR$_6$R$_7$, or R$_{1a}$, R$_{1b}$, R$_{1c}$ are bound respectively to R$_{2a}$, R$_{2b}$, R$_{2c}$ and to the carbon atom that bears them and represent —O-alkyl-O—;
R$_3$ represents a hydrogen atom or an alkyl group,
R$_4$ represents a group —CONR$_6$R$_7$; hydroxy-alkyl substituted with a haloalkyl group; -alkyl-NH—SO$_2$-alkyl; —NH—SO$_2$-alkyl; —O—SO$_2$—NR$_6$R$_7$; -alkyl-CO—NR$_6$R$_7$; —O-alkyl-CO—NR$_6$R$_7$; -alkyl-NR$_6$R$_7$; —O—CO—NR$_6$R$_7$; alkyl-heteroaryl; heteroaryl optionally substituted with an alkyl group; alkoxy-imino; —CO—NH—NH—CO-alkyl; provided that R$_4$ is in cis position relative to the urea substituent on the adamantyl ring when it represents the group —CONR$_6$R$_7$ and that R$_6$ and R$_7$ each represent hydrogen, an -alkyl or -alkyl-phenyl group;
R$_5$ represent hydrogen, an alkyl group or an -alkyl-phenyl group;
R$_6$ and R$_7$, each independently represent a hydrogen atom, an alkyl or alkoxy group or an -alkyl-phenyl group, and
R$_8$ represents a hydrogen atom, an alkyl group or a group of formula —B-Het, where B can be absent or can represent a bond, an oxygen atom or a —CO— or —SO$_2$—(CH$_2$)$_n$ group wherein n is 0, 1 or 2 and where Het represents a heteroaryl or a heterocycloalkyl optionally substituted with 1 to 3 groups selected from the alkyl, —SO$_2$-alkyl and —COOR$_5$ groups,
or a pharmaceutically acceptable salt thereof.

2. The compound of claim 1, wherein Ar$_1$ represents a heteroaryl group.
3. The compound of claim 2, wherein Ar$_1$ represents a pyridinyl group.
4. The compound of claim 1, wherein Ar$_2$ represents a heterocycloalkyl group.
5. The compound of claim 4, wherein Ar$_2$ represents a piperazinyl group.
6. The compound of claim 1, wherein A represents a bond.
7. The compound of claim 1, wherein R$_{1a}$, R$_{2a}$, R$_{1b}$ and R$_{2b}$, each represent a hydrogen atom.
8. The compound of claim 1, wherein R$_{1c}$ and R$_{2c}$, each independently represent a hydrogen atom, an alkyl or —SO$_2$-cycloalkyl group.
9. The compound claim 1, wherein R$_{1a,1b}$ and R$_{2a,2b,2c}$ each independently represent a hydrogen atom and R$_{1c}$ represents hydrogen, an alkyl, or —SO$_2$-cycloalkyl group.
10. The compound of claim 1, wherein R$_3$ represents a hydrogen atom.
11. The compound of claim 1, wherein R$_8$ represents a hydrogen atom or a group of formula —B-Het, where B can be absent and Het represents a tetrahydropyranyl group.
12. The compound of claim 1, wherein:
A is a bond;
Ar$_1$ is a heteroaryl;
Ar$_2$ is a heterocycloalkyl;
R$_3$ represents a hydrogen atom or an alkyl,
R$_4$ represents a group —CONR$_6$R$_7$; hydroxy-alkyl substituted with a haloalkyl group; -alkyl-NH—SO$_2$-alkyl; —NH—SO$_2$-alkyl; —O—SO$_2$—NR$_6$R$_7$; -alkyl-CO—NR$_6$R$_7$; —O-alkyl-CO—NR$_6$R$_7$; -alkyl-NR$_6$R$_7$; —O—CO—NR$_6$R$_7$; alkyl-heteroaryl; heteroaryl optionally substituted with an alkyl group;
alkoxy-imino; —CO—NH—NH—CO-alkyl; provided that R$_4$ is in cis position relative to the urea substituent on the adamantyl ring when it represents the group —CONR$_6$R$_7$ and that R$_6$ and R$_7$ each represent hydrogen, an -alkyl or -alkyl-phenyl group;
R$_5$ represent hydrogen, an alkyl group or an -alkyl-phenyl group;
R$_6$ and R$_7$, each independently represent a hydrogen atom, an alkyl or alkoxy group or an -alkyl-phenyl group, and
R$_8$ represents a hydrogen atom; an alkyl group or a tetrahydropyranyl group.
13. The compound of claim 1, wherein R$_{1a,1b,1c}$ and R$_{2a,2b,2c}$ are hydrogen and R$_8$ is an alkyl or tetrahydropyranyl group.
14. The compound of claim 1, wherein R$_{1a,1b,1c}$ and R$_{2a,2b}$ and R$_8$ are hydrogen and R$_{2c}$ is an —SO$_2$-cycloalkyl group.
15. A pharmaceutical composition comprising the compound of claim 1, or a pharmaceutically acceptable salt thereof; and at least one pharmaceutically acceptable excipient.
16. A method of modulating 11β-hydroxysteroid dehydrogenase type 1 activity in a patient in need thereof, comprising administering to said patient a therapeutically effective amount of the compound according to claim 1.

According to another of its aspects, the present invention also relates to a method of treatment of the pathologies stated above, comprising the administration, to a patient, of an effective dose of a compound according to the invention, or a pharmaceutically acceptable salt or hydrate or solvate thereof.

17. A method of preparing the compound of claim 1, wherein a compound of formula (IV):

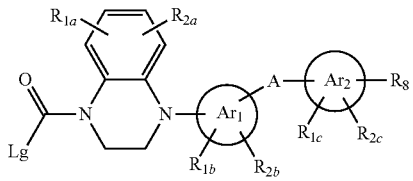
(IV)

where Lg is selected from the group consisting of halogens, mesyl, tosyl, triflate, acetyl, paranitrophenyl, trichloromethoxy, imidazole and methyl-imidazolium a group which can be easily cleaved from the compound of formula (IV) by rupture of a heterolytic bond with departure of an electron pair; is reacted with a compound of formula (V):

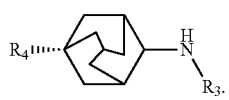
(V)

18. The method according to claim 17, wherein Lg is chloro.

19. A method of preparing the compound of claim 1 in which $R_4$ is a hydroxy-alkyl group substituted with a haloalkyl comprising:

1) reducing the ester function of a compound of formula (IX):

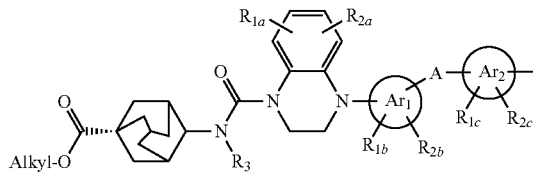
(IX)

to an alcohol function to form a compound of formula (X):

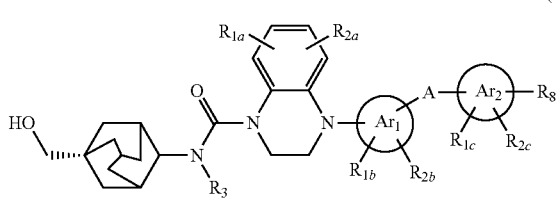
(X)

2) oxidizing the alcohol function of the compound of formula (X) to an aldehyde function to obtain a compound of formula (XI):

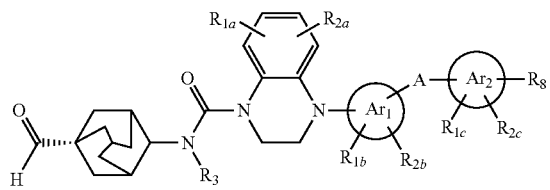
(XI)

3) adding a haloalkyl group onto the aldehyde function of the compound of formula (XI) to form the compound of formula (VIII):

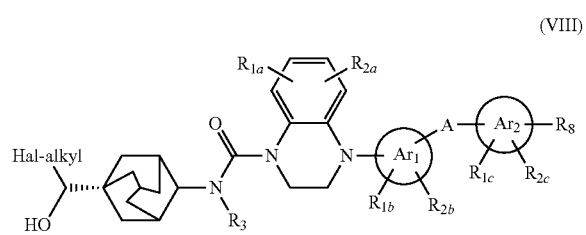
(VIII)

in which Hal-alkyl denotes a haloalkyl group.

20. A method of preparing the compound of claim 1 in which $R_4$ is a group O—CO—$NR_6R_7$ comprising reacting a of formula (XIII):

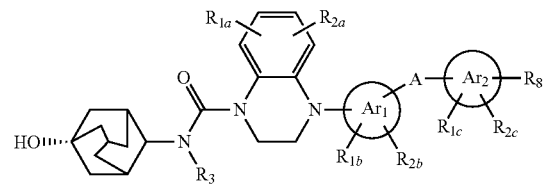
(XIII)

with an isocyanate or a carbamoyl chloride in the presence or absence of a base.

21. A method of preparing the compound of claim 1 in which $R_4$ is a group —CO—$NR_6R_7$ comprising reacting a compound of formula (XXXIII):

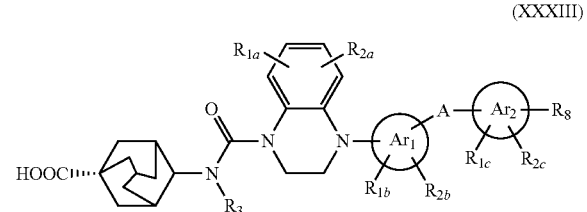
(XXXIII)

with an amine of formula $HNR_6R_7$.

22. A method of preparing the compound of claim 1 in which $R_4$ represents a 1,2,4-oxadiazole group comprising reacting an acid of formula (XXXIII):

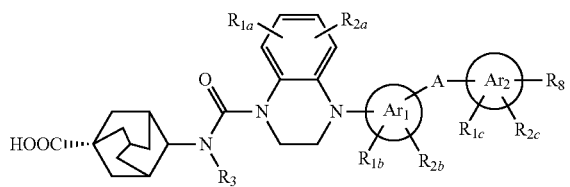

(XXXIII)

with a hydroamidine of formula (LII):

(LII)

in the presence of a coupling agent selected from the group consisting of O-benzotriazol-1-yl-N,N,N',N'-tetramethyluronium tetrafluoroborate, N,N'-diisopropylcarbodiimide, N,N'-dicyclohexylcarbodiimide and 1-(3-dimethylaminopropyl)-3-ethylcarbodiimide; and a base.

23. The compound of formula (I) as claimed in claim 1 selected from: Cis 4-{5-[4-(Tetrahydro-pyran-4-yl)piperazin-1-yl]pyridin-2-yl}-3,4-dihydro-2H-quinoxaline-1-carboxylic acid (5-carbamoyl-adamantan-2-yl)amide;

Trans 4-[5-(4-tert-Butyl-piperazin-1-yppyridin-2-yl]-3,4-dihydro-2H-quinoxaline-1-carboxylic acid[5-(methanesulfonylamino-methyl)adamantan-2-yl]amide;

Trans 4-[5-(4-Cyclopropanesulfonyl-piperazin-1-yl)pyridin-2-yl]-3,4-dihydro-2H-quinoxaline-1-carboxylic acid (5-carbamoylmethyl-adamantan-2-yl)amide;

Trans 4-[5-(4-Cyclopropanesulfonyl-piperazin-1-yl)pyridin-2-yl]-3,4-dihydro-2H-quinoxaline-1-carboxylic acid (5-aminomethyl-adamantan-2-yl)amide;

Trans Carbamic acid 4-({4-[5-(4-cyclopropanesulfonyl-piperazin-1-yl)pyridin-2-yl]-3,4-dihydro-2H-quinoxaline-1-carbonyl}amino)adamantan-1-yl ester;

Trans 4-[5-(4-tert-Butyl-piperazin-1-yl)pyridin-2-yl]-3,4-dihydro-2H-quinoxaline-1-carboxylic acid[5-(2,2,2-trifluoro-1-hydroxy-ethyl)adamantan-2-yl]amide;

Trans 4-[5-(4-tert-Butyl-piperazin-1-yl)pyridin-2-yl]-3,4-dihydro-2H-quinoxaline-1-carboxylic acid[5-(2H-tetrazol-5-ylmethyl)adamantan-2-yl]amide;

Trans 4-[5-(4-Cyclopropanesulfonyl-piperazin-1-yl)pyridin-2-yl]-3,4-dihydro-2H-quinoxaline-1-carboxylic acid (5-methoxycarbamoyl-adamantan-2-yl)amide;

Trans 4-[5-(4-tert-Butyl-piperazin-1-yl)pyridin-2-yl]-3,4-dihydro-2H-quinoxaline-1-carboxylic acid (5-methanesulfonylamino-adamantan-2-yl)amide; and Trans 4-[5-(4-Cyclopropanesulfonyl-piperazin-1-yl)pyridin-2-yl]-3,4-dihydro-2H-quinoxaline-1-carboxylic acid [5-(3-methyl-[1,2,4]oxadiazol-5-yl)adamantan-2-yl]amide.

* * * * *